(12) United States Patent
Takamizawa

(10) Patent No.: US 8,034,165 B2
(45) Date of Patent: Oct. 11, 2011

(54) SINGLE-CRYSTALLINE ORGANIC CARBOXYLIC ACID METAL COMPLEX, PROCESS FOR PRODUCING THE SAME, AND USE THEREOF

(75) Inventor: Satoshi Takamizawa, Yokohama (JP)

(73) Assignee: Yokohama City University, Yokohama-shi, Kanagawa (JP)

( * ) Notice: Subject to any disclaimer, the term of this patent is extended or adjusted under 35 U.S.C. 154(b) by 539 days.

(21) Appl. No.: 11/921,681

(22) PCT Filed: May 10, 2006

(86) PCT No.: PCT/JP2006/309429
§ 371 (c)(1), (2), (4) Date: May 8, 2008

(87) PCT Pub. No.: WO2006/132049
PCT Pub. Date: Dec. 14, 2006

(65) Prior Publication Data
US 2009/0139401 A1    Jun. 4, 2009

(30) Foreign Application Priority Data

Jun. 9, 2005  (JP) .................. 2005-169081
Jun. 9, 2005  (JP) .................. 2005-169083
Jun. 9, 2005  (JP) .................. 2005-169087

(51) Int. Cl.
*B01D 53/02* (2006.01)
(52) U.S. Cl. ............. 95/141; 95/116; 95/133; 95/134; 96/90; 117/106; 428/220; 544/225; 544/226
(58) Field of Classification Search .......... 95/116, 95/133, 134; 117/106; 428/220; 544/225, 544/226
See application file for complete search history.

(56) References Cited

FOREIGN PATENT DOCUMENTS

| JP | 2000063393 A | * | 2/2000 |
|---|---|---|---|
| JP | 2000-109485 A | | 4/2000 |
| JP | 2000-309592 A | | 11/2000 |
| JP | 2004-196594 A | | 7/2004 |
| JP | 2005-232109 A | | 9/2005 |
| JP | 2005-255651 A | | 9/2005 |

OTHER PUBLICATIONS

Translation of JP 2000-063393 A, Feb. 2000, Japan, Seki et al.*  Mori Wasuke, Synthesis and Gas Occlusion of Rhodium(II) Benzoate Bridged by Pyrazine Derivatives; Mo. Cryst. Liq. Cryst., 2000, vol. 342, pp. 193-198.*
STIC search results dated May 7, 2010.*

* cited by examiner

*Primary Examiner* — Robert J. Hill, Jr.
*Assistant Examiner* — Christopher Jones
(74) *Attorney, Agent, or Firm* — Birch, Stewart, Kolasch & Birch, LLP

(57) ABSTRACT

A large single crystal of a complex such as an organic carboxylic acid metal complex, which crystal is useful as an adsorbent of various gases and vapors of organic solvents and as a hydrogen-absorbing material, as well as a process for producing the crystal, is disclosed. Two layers wherein an upper layer thereof is constituted by a solution containing a metal salt and an organic carboxylic acid having a conjugated system, or a solution containing a metal salt of the organic carboxylic acid having a conjugated system, and wherein a lower layer of the two layers is constituted by a solvent which is not miscible with the solvent of the solution, is formed. Vapor of pyrazine or a substituted pyrazine from a solution of pyrazine or the substituted pyrazine is introduced into the upper layer to allow reaction, thereby forming a large single crystal(s) of the organic carboxylic acid metal complex at the interface between the two layers, which crystal(s) has(have) a longer side with a size of not less than 0.8 mm.

6 Claims, 22 Drawing Sheets

SINGLE-CRYSTALLINE ORGANIC CARBOXYLIC ACID METAL COMPLEX, PROCESS FOR PRODUCING THE SAME, AND USE THEREOF

TECHNICAL FIELD

The present invention relates to a single-crystalline organic carboxylic acid metal complex, production process thereof and uses thereof.

BACKGROUND ART

Patent Literature 1 discloses a carboxylic acid complex composed of benzoic acid, a metal, and an organic ligand which can coordinate with the metal by bidentate coordination, and also discloses that the complex is useful as a methane gas-absorbing material. Non-patent Literatures 1 and 2 disclose a single crystal of one-dimensionally linked organic metal complex composed of benzoic acid, rhodium (Non-patent Literature 1) or copper (Non-patent Literature 2), and pyrazine, and also disclose that the crystal structure of the metal complex changes when the metal complex adsorbs or desorbs carbon dioxide molecules which are guest molecules. On the other hand, as an adsorbent of vapors of organic solvents such as benzene and toluene, active carbon, zeolite and the like are conventionally used (Patent Literatures 2 and 3). As a hydrogen-absorbing material, alloys and sintered bodies thereof have been used (Patent Literatures 4 and 5).

Patent Literature 1: JP 2000-309592 A
Patent Literature 2: JP 2004-255336 A
Patent Literature 3: JP 2004-261780 A
Patent Literature 4: JP 2003-1389 A
Patent Literature 5: JP 2003-3203 A
Non-patent Literature 1: Satoshi Takamizawa et al., Angew. Chem. Int. Ed. 2003, 42, 4331-4334
Non-patent Literature 1: Satoshi Takamizawa et al., Inorganic Chemistry Communications, Volume 6, Issue 10, October 2003, pp. 1326-1328

DISCLOSURE OF THE INVENTION

Problems to be Solved by the Invention

An object of the present invention is to provide a large crystal of the complex such as the organic carboxylic acid complex described in Non-patent Literature 1, which is useful as an adsorbent of various gases and vapors of organic solvents, or as a hydrogen-absorbing material or the like, as well as a production process thereof.

Another object of the present invention is to provide an adsorbent of volatile organic compounds, which easily adsorbs and desorbs vapors of organic solvents such as benzene and toluene, and harmful organic compounds such as formaldehyde continuously even without a regeneration treatment. Another object of the present invention is to provide a hydrogen-absorbing material which easily adsorbs and desorbs hydrogen, and which can absorb a large amount of hydrogen per a unit volume.

Still another object of the present invention is to provide a novel organic metal complex having a novel chemical structure and physical properties different from those of the organic metal complexes described in the above-mentioned prior art references, and which is useful for adsorption and desorption of various gases, as well as a gas-absorbing material comprising the complex.

Means for Solving the Problems

The present inventor intensively studied to discover that a large single crystal(s) of an organic carboxylic acid metal complex can be grown by forming two layers wherein an upper layer thereof is constituted by a solution containing a metal salt and an organic carboxylic acid having a conjugated system, or a solution containing a metal salt of the organic carboxylic acid having a conjugated system, and wherein a lower layer of the two layers is constituted by a solvent which is not miscible with the solvent of the solution; and introducing vapor of pyrazine or a substituted pyrazine from a solution of pyrazine or the substituted pyrazine into the upper layer to allow reaction, thereby forming a large single crystal(s) of the organic carboxylic acid metal complex at the interface between the two layers, thereby completing the present first invention.

That is, the present invention provides a process for producing a large single crystal(s) of an organic carboxylic acid metal complex constituted by recurring units of the Formula [I]:

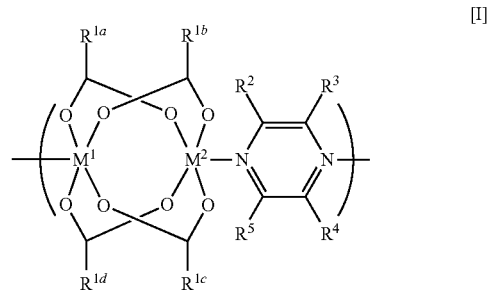

(wherein $M^1$ and $M^2$ are each independently a metal which can be bivalent; $R^{1a}$, $R^{1b}$, $R^{1c}$ and $R^{1d}$ are each independently an organic group having a conjugated system; $R^2$, $R^3$, $R^4$ and $R^5$ are each independently hydrogen, $C_1$-$C_4$ alkyl or $C_1$-$C_4$ alkenyl), the process comprising the steps of: forming two layers wherein an upper layer thereof is constituted by a solution containing a salt of the metal which can be bivalent and the organic carboxylic acid having the conjugated system, or a solution containing a metal salt of the organic carboxylic acid having the conjugated system, the metal constituting the metal salt being the metal which can be bivalent, and wherein a lower layer of the two layers is constituted by a solvent which is not miscible with the solvent of the solution; introducing, in this state, into the upper layer vapor of pyrazine or a substituted pyrazine from a solution of pyrazine or the substituted pyrazine to allow reaction, thereby forming a single crystal(s) of the organic carboxylic acid metal complex at the interface between the two layers.

The present inventor intensively studied to discover that an organic carboxylic acid metal complex having a specific structure easily adsorbs vapors of organic solvents and easily desorbs the vapors even without a special regeneration treatment, and that the organic carboxylic acid metal complex easily adsorbs and desorbs hydrogen, and the amount of absorbed hydrogen per a unit volume is large, thereby completing the present second invention.

That is, the present invention provides an adsorbent of volatile organic compounds, the adsorbent comprising an organic carboxylic acid metal complex constituted by recurring units of the above-described Formula [I] (wherein in Formula [I], $M^1$ and $M^2$; $R^{1a}$, $R^{1b}$, $R^{1c}$ and $R^{1d}$; and $R^2$, $R^3$, $R^4$ and $R^5$ have the same meanings as described above). The present invention also provides a use of the organic carboxylic acid complex of the present invention for the production of an adsorbent of volatile organic compounds. The present invention further provides a method for adsorbing a volatile organic compound(s), the method comprising contacting the organic carboxylic acid metal complex according to the present invention with a vapor(s) of a volatile organic compound(s).

The present invention further provides an agent for maintaining concentration of a volatile organic compound(s) in the air at a level not higher than a prescribed level, the agent comprising the organic carboxylic acid metal complex according to the present invention. The present invention still further provides a use of the organic carboxylic acid metal complex according to the present invention, for the production of an agent for maintaining concentration of a volatile organic compound(s). The present invention still further provides a method for maintaining concentration of a volatile organic compound(s) at a level not higher than a prescribed level, the method comprising placing in the air the adsorbent of volatile organic compounds according to the present invention. The present invention still further provides a hydrogen-absorbing material comprising the organic carboxylic acid metal complex according to the present invention. The present invention still further provides a use of the organic carboxylic acid metal complex according to the present invention described above, for the production of a hydrogen-absorbing material. The present invention still further provides a method for absorbing hydrogen gas, the method comprising contacting the organic carboxylic acid metal complex according to the present invention described above. The present invention still further provides a method for one-dimensionally aligning metal atoms in a single line, the method comprising absorbing a metal vapor with the organic carboxylic acid metal complex, and an organic carboxylic acid complex produced by this process, the organic carboxylic acid complex harboring in a channel structure metal atoms as a guest, the metal atoms being aligned one-dimensionally in a single line.

Further, the present inventor intensively studied to discover that by introducing a specific substituent(s) on the pyrazine ring of an organic carboxylic acid metal complex composed of a carboxylic acid, a metal which can be bivalent and pyrazine, the crystal structure and the physical properties of the complex can be changed when compared to the unsubstituted complex, and various organic carboxylic acid metal complexes and gas-absorbing materials having different adsorption characteristics to various gases can be provided, thereby completing the present third invention.

That is, the present invention provides an organic carboxylic acid metal complex constituted by recurring units of the above-described Formula [I] (wherein in Formula [I], $M^1$ and $M^2$; $R^{1a}$, $R^{1b}$, $R^{1c}$ and $R^{1d}$; and $R^2$, $R^3$, $R^4$ and $R^5$ have the same meanings as described above, with the proviso that $R^2$, $R^3$, $R^4$ and $R^5$ are not simultaneously hydrogen atoms).

The present invention also provides a gas-absorbing material comprising the organic carboxylic acid metal complex according to the present invention described above. The present invention further provides a gas-adsorbing permeable membrane comprising the single crystal of the organic carboxylic acid metal complex according to the present invention described above.

The present invention also provides a single crystalline organic carboxylic acid metal complex constituted by recurring units of the above-described Formula [I] (wherein in Formula [I], $M^1$ and $M^2$; $R^{1a}$, $R^{1b}$, $R^{1c}$ and $R^{1d}$; and $R^2$, $R^3$, $R^4$ and $R^5$ have the same meanings as described above), which single crystal has a size of a longer side of not less than 1 μm.

Effects of the Invention

By the present first invention, a large single crystal of an organic carboxylic acid metal complex useful as an adsorbent of various gases and vapors of organic solvents, as well as a production process thereof, was first provided. When the complex is used as an adsorbent of various gases and vapors of organic solvents, as a hydrogen-absorbing material or the like, if large single crystals are used, the amount of adsorption per a unit apparent volume can be increased, which is advantageous. Further, a large single crystal can be used as it is as an adsorption filter of various gases and vapors of organic solvents.

By the present second invention, a novel adsorbent of volatile organic compound vapors and a hydrogen-absorbing material, comprising an organic carboxylic acid metal complex having a specific structure, were provided. With the adsorbent of organic solvent vapors according to the present invention, when the concentration of the vapor of the organic solvent exceeds a prescribed level, the crystal structure of the organic carboxylic acid metal complex changes and the adsorption amount is drastically increased, so that the concentration of the organic solvent vapor in the air can be maintained at a level not higher than the concentration at which the adsorption amount is drastically increased (hereinafter referred to as "critical concentration"). Further, since the adsorption and desorption of the organic solvent vapor is quick and reversible, when the concentration of the organic solvent vapor in the air decreases to a level lower than the critical concentration by ventilation or the like, the organic solvent vapor adsorbed by the adsorbent is quickly desorbed. Therefore, the adsorbent continuously retains the ability as an adsorbent without any special regeneration treatment such as heat treatment or the like. The hydrogen-absorbing material according to the present invention easily adsorb and desorb hydrogen, and the amount of the absorbed hydrogen per a unit volume is large, so that it is suited for storage of hydrogen.

Further, by the present third invention, an organic carboxylic acid metal complex having a novel chemical structure and a gas-absorbing material using the same were provided. According to the present invention, by binding a specific substituent(s) on the pyrazine ring of the organic carboxylic acid metal complex, various organic carboxylic acid metal complexes and gas-absorbing materials having different crystal structures, and in turn, having different adsorption and desorption characteristics to various gases are provided.

BEST MODE FOR CARRYING OUT THE INVENTION

Figure 1:
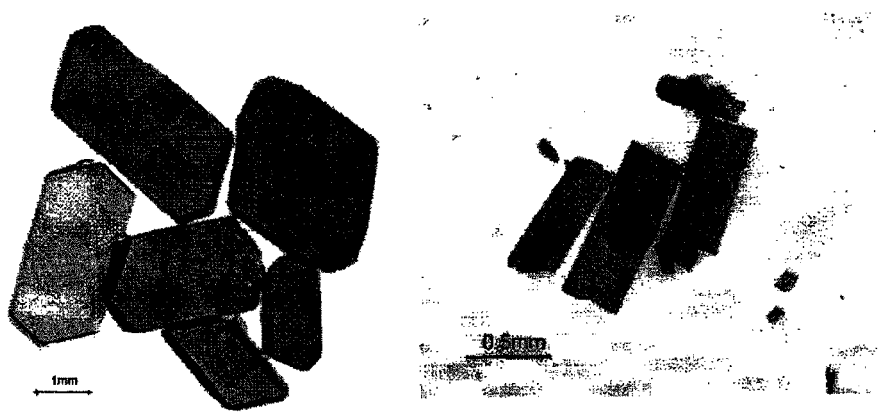
FIG. 1 are schematic views of the stereoscopic micrographs of the large single crystals obtained in Examples 1 and 2.

As described above, the organic carboxylic acid metal complex used in the present first invention is constituted by recurring units of the above-described Formula [I]. In Formula [I], the bond between $M^1$ and O, the bond between $M^2$ and O, the bond between $M^1$ and $M^2$, and the bond between $M^2$ and N are coordinate bonds. The number of the recurring units represented by Formula [I] is not restricted, and usually $10^7$ to $10^{10}$, preferably about $8 \times 10^7$ to $10^9$. As is apparent from Formula [I], among the 4 oxygen atoms bound to $M^1$, the right upper oxygen atom is bound to the carbon atom to which $R^{1b}$ is bound, and the right lower oxygen atom is bound to the carbon atom to which $R^{1c}$ is bound. Similarly, among the 4 oxygen atoms bound to $M^2$, the left upper oxygen atom is bound to the carbon atom to which $R^{1a}$ is bound, and the left lower oxygen atom is bound to the carbon atom to which $R^{1d}$ is bound.

In Formula [I], $M^1$ and $M^2$ are each independently a metal which can be bivalent, and may be a transition metal or a typical metal. Preferred examples of M include manganese, iron, cobalt, nickel, copper, zinc, ruthenium, rhodium, chromium, molybdenum, palladium and tungsten. Among these metals, copper and rhodium are especially preferred. $M^1$ and $M^2$ preferably are the same kind of metal atom.

In Formula [I], $R^{1a}$, $R^{1b}$, $R^{1c}$ and $R^{1d}$ ($R^{1a}$, $R^{1b}$, $R^{1c}$ and $R^{1d}$ is also collectively hereinafter referred to as "$R^1$") are each independently an organic group having a conjugated system, that is, for example, an organic group containing a benzene ring, naphthalene ring, anthracene ring or a hetero ring thereof, and a phenyl group which is optionally substituted, and especially, unsubstituted phenyl group is preferred. In cases where the phenyl group is substituted, examples of the substituents include $C_1$-$C_4$ alkyl, $C_1$-$C_4$ haloalkyl, hydroxyl, amino, cyano, $C_1$-$C_4$ monoalkylamino, $C_1$-$C_4$ alkoxyl, halogen and phenyl which is optionally substituted (the substituents are the same as described above (excluding substituted phenyl), and the number of substituents is 1 to 5. Unless otherwise specified, in the present description, "alkyl" includes both linear alkyl and branched alkyl. "Alkenyl" and "alkoxyl" also include linear and branched groups. $R^{1a}$, $R^{1b}$, $R^{1c}$ and $R^{1d}$ are preferably the same kind of organic group.

In Formula [I], $R^2$, $R^3$, $R^4$ and $R^5$ are each independently hydrogen, $C_1$-$C_4$ alkyl or $C_1$-$C_4$ alkenyl. Preferred examples thereof include methyl, ethyl, propyl, allyl and the like. Two to 4 of $R^2$, $R^3$, $R^4$ and $R^5$ are preferably hydrogen atoms.

The recurring units each represented by the above-described Formula [I] are one-dimensionally linked, and the molecules gather together to form a molecular crystal. In forming the crystal, since the conjugated systems in $R^1$ are closely located, π-π bonds are formed and the crystal structure is stabilized.

A large single crystal of the organic carboxylic acid metal complex can be prepared by forming two layers wherein an upper layer thereof is constituted by a solution containing a salt of the metal (in cases where $M^1$ and $M^2$ are different, two kinds of metal salts, this provision being also applied hereinafter) which can be bivalent and the organic carboxylic acid ($R^1$—COOH (wherein $R^1$ has the same meaning as described above; in cases where $R^{1a}$, $R^{1b}$, $R^{1c}$ and $R^{1d}$ are a plurality of organic groups, a plurality of kinds of organic groups, this provision being also applied hereinafter) having the conjugated system, or a solution containing a metal salt of the organic carboxylic acid ($R^1$—COOH (wherein $R^1$ has the same meaning as described above)) having the conjugated system, the metal constituting the metal salt being the metal which can be bivalent, and wherein a lower layer of the two layers is constituted by a solvent which is not miscible with the solvent of the solution; and introducing, in this state, into the upper layer vapor of pyrazine or a substituted pyrazine from a solution of pyrazine or the substituted pyrazine to allow reaction, thereby forming a single crystal(s) of the organic carboxylic acid metal complex at the interface between the two layers.

Here, as the above-described metal salt, acetic acid salt, formic acid salt, sulfuric acid salt and carbonic acid salt are preferred, and acetic acid salt is especially preferred. As the solvent of the solution of the metal salt and the above-described organic carboxylic acid, or as the solvent of the solution of the metal salt of the organic carboxylic acid, methanol, ethanol, propanol, acetonitrile, dimethylformamide, nitromethane, tetrahydrofuran, methyl acetate and the like are preferred. The concentration of the metal salt (in cases where a plurality of kinds of metal salts are contained, the total thereof) in the solution is not restricted, and is usually about 0.00001 to 0.5 $molL^{-1}$, preferably about 0.001 to 0.1 $molL^{-1}$. The concentration of the organic carboxylic acid (in cases where a plurality of kinds of organic carboxylic acids are contained, the total thereof) is not restricted, and is usually about 0.0001 to 1 $molL^{-1}$, preferably about 0.004 to 0.4 $molL^{-1}$. In cases where a metal salt of an organic carboxylic acid is used, the concentration thereof is not restricted, and is usually about 0.00001 to 1 $molL^{-1}$, preferably about 0.001 to 0.1 $molL^{-1}$.

The solvent constituting the above-described lower layer is not restricted and may be any solvent which is not miscible with the solvent of the solution of the upper layer, whose density (preferably not less than 1.5) is larger than the solvent in the upper layer, and which does not react with the respective reactants and the formed complex. The term "is not miscible" herein means that the interface between the two layers clearly exists even after the crystal growth reaction over several tens of days. In cases where the solvent in the solution of the upper layer is methanol or acetonitrile, the preferred solvents constituting the lower layer are fluorine-containing solvents. Examples of the fluorine-containing solvents include perfluorodecahydrophenanthrene, perfluorodecaline, perfluoro-1-methyldecaline, perfluorodimethylnaphtalene, perfluoro-1,3-dimethylcyclohexane, 2,5-dichlorobenzotrifluoride, chloropentafluorobenzene, 1,1,2-trichloro-1,2,2-trifluoroethane (e.g., trade name "Flonsolve" produced by Asahi Glass Co., Ltd.), hexafluorobenzene, 1,3-di-trifluoromethylbenzol, 2,2,2-trifluoroethanol, trifluoromethylbenzene, trade name "PF5052" produced by Sumitomo 3M Limited, perfluoro-2-normalbutylfuran-based solvents (e.g., trade name "Florinate FC75" produced by Sumitomo 3M Limited), trisperfluoro n-butylamine-based solvents (e.g., trade name "Florinate FC43" produced by Sumitomo 3M Limited), trisperfluoroalkylamine-based solvents (e.g., trade name "Florinate FC3283", "Florinate FC40" and "Florinate FC70"), all of which are produced by Sumitomo 3M Limited), Garden DO2 (trade name) produced by Japan Montedison and chlorofluorocarbon (e.g., trade name "Fron 113" produced by Asahi Glass Co., Ltd).

Into the solution constituting the upper layer, vapor of pyrazine or a substituted pyrazine from a solution of pyrazine or the substituted pyrazine is introduced to allow reaction. Pyrazine or the substituted pyrazine is not directly used, but pyrazine or the substituted pyrazine is dissolved in a solvent to prepare a solution, and the vapor of pyrazine or the substituted pyrazine generated from the solution is subjected to the reaction. By so doing, the vapor pressure of pyrazine or the substituted pyrazine and, in turn, the amount of the pyrazine or the substituted pyrazine introduced per a unit time can be decreased. To make the amount of the pyrazine or the substituted pyrazine introduced per a unit time small, it is preferred to introduce the vapor by natural diffusion at the reaction temperature. As the solvent of pyrazine or the substituted pyrazine, organic solvents whose vapor pressure is low, such as ethylene glycol and xylene are preferred. The concentration of pyrazine or the substituted pyrazine in the solution is not restricted, and is preferably about 0.00001 to 0.01 $molL^{-1}$, more preferably about 0.0001 to 0.01 $molL^{-1}$.

The reaction temperature is not restricted and is preferably about 10° C. to 25° C. The reaction time is preferably about 15 days to 2 months. Although the reaction vessel is not restricted at all, in order that the produced single crystal(s) is(are) not adhered to the wall of the vessel, a vessel whose surface has been subjected to an anti-adhesion treatment, such as Teflon (registered trademark)-coating, is preferably used.

By the above-described method, a single crystal(s) of the above-described organic carboxylic acid metal complex is(are) generated and grown at the interface between the two layers. Although the size of the single crystal is not restricted, one whose longer side is not shorter than 0.8 mm is preferred. In the Examples below, a crystal whose longer side is 5 mm was obtained. By extending the reaction time, a crystal whose longer side is about 10 mm can be obtained. The term "longer side" herein means the longest side in the polygon whose area is the largest of the surfaces constituting the crystal. The organic carboxylic acid metal complex represented by above-described Formula [I] whose longer side is not shorter than 0.8 mm was not known before the present application, so that such a large single crystal per se is novel. Thus, the present invention also provides a single crystal of the organic carboxylic acid metal complex represented by above-described Formula [I], whose longer side is not shorter than 0.8 mm.

The large single crystal obtained by the method of the present invention can be used, similar to single crystals having an ordinary size, as an adsorbent of various gases and organic solvents, as a hydrogen-absorbing material and the like.

As described above, the present second invention provides an adsorbent of volatile organic compounds, the adsorbent comprising an organic carboxylic acid metal complex constituted by recurring units of the above-described Formula [I] (wherein in Formula [I], $M^1$ and $M^2$; $R^{1a}$, $R^{1b}$, $R^{1c}$ and $R^{1d}$; and $R^2$, $R^3$, $R^4$ and $R^5$ have the same meanings as described above). As the explanations about $M^1$ and $M^2$; $R^{1a}$; $R^{1b}$; $R^{1c}$ and $R^{1d}$; and $R^2$, $R^3$, $R^4$ and $R^5$ in Formula [I] and preferred examples thereof, the above-described explanations and preferred examples are equally applied as they are. The number of the recurring units represented by Formula [I] is not restricted, and usually 10 to $10^8$, preferably about $10^2$ to $10^7$. However, in cases where the organic carboxylic acid metal complex represented by Formula [I] is in the form of the large single crystal produced by the method according to the present first invention, the number of the recurring units is usually $10^7$ to $10^{10}$, preferably about $8\times10^7$ to $10^9$ as described above.

The recurring units each represented by Formula [I] are one-dimensionally linked and the molecules gather together to form a molecular crystal. In forming the crystal, since the conjugated systems in $R^1$ are closely located, π-π bonds are formed and the crystal structure is stabilized. The molecular crystal is preferably a single crystal. The single crystal has advantages in that not only the amount of the adsorbed organic solvent vapor or hydrogen per a unit volume is large, but also uniformity of the physical properties can be attained, so that complexes having prescribed physical properties can be produced with high reproducibility. Further, by the method according to the present first invention, a large single crystal whose longer side is not shorter than 0.8 mm can be produced. Use of such a large single crystal is advantageous because the amount of adsorbed vapor or the amount of the absorbed hydrogen per a unit apparent volume can be made large.

The above-described organic carboxylic acid metal complex can be produced by reacting a metal salt (in cases where $M^1$ and $M^2$ are different, two kinds of metal salts, this provision being also applied hereinafter), an organic carboxylic acid ($R^1$—COOH (wherein $R^1$ has the same meaning as described above; in cases where $R^{1a}$, $R^{1b}$, $R^{1c}$ and $R^{1d}$ are a plurality of organic groups, a plurality of kinds of organic groups, this provision being also applied hereinafter), and a substituted pyrazine slowly in a solvent. By this process, single crystals of the organic carboxylic acid metal complex according to the present invention can be produced. Alternatively, the complex can be produced by reacting a metal salt of the organic carboxylic acid ($R^1$—COOH (wherein $R^1$ has the same meaning as described above) with a substituted pyrazine in a solvent. As the solvent, methanol and acetonitrile are preferred. As the metal salt, acetic acid salt, formic acid salt, sulfuric acid salt, nitric acid salt and carbonic acid salt are preferred, and acetic acid salt is especially preferred. The reaction temperature is not restricted, and good results are obtained at room temperature, although the reaction can be carried out at about 0° C. to 70° C. The reaction time is not restricted, and usually, good results are obtained when the reaction time is about 3 hours to 1 week. The ratio of the metal salt to the organic carboxylic acid to be reacted is not restricted, and is usually about 1:2 to 1:8 by mole, and the ratio of the metal salt to the substituted pyrazine is usually about 1:0.5 to 1:10 by mole. Preferred examples of the production process are described in detail in the Examples below.

Further, large single crystals constituted by the recurring units each represented by Formula [I] can be produced by the method according to the present first invention described above, and such large single crystals may preferably be applied to the use of the present second invention, that is, as an adsorbent of volatile organic compounds and as a hydrogen-absorbing material.

The organic carboxylic acid metal complex forms a molecular crystal, and in the molecular crystal, one-dimensionally extending voids (channel structures) or regularly arranged spaces exist. In the intracrystal spaces, gas can be adsorbed and desorbed as a guest. The adsorbent of volatile organic compounds according to the present invention comprises the above-described organic carboxylic acid metal complex. As will be concretely shown in the Examples below, with the adsorbent of volatile organic compounds according to the present invention, when the concentration of the vapor of the organic solvent exceeds a prescribed level, the crystal structure of the organic carboxylic acid metal complex changes and the adsorption amount is drastically increased. Therefore, the concentration of the organic solvent vapor in the air can be maintained at a level not higher than the concentration at which the adsorption amount is drastically increased (hereinafter referred to as "critical concentration"). Thus, by placing the adsorbent of volatile organic compounds according to the present invention in the air, the concentration of the vapor of the organic solvent can be maintained at a level not higher than the prescribed level. Thus, the adsorbent of volatile organic compounds according to the present invention may be used as an agent for maintaining concentration of a volatile organic compound(s) in the air at a level not higher than a prescribed level. Further, since the adsorption and desorption of the organic solvent vapor is quick and reversible, when the concentration of the organic solvent vapor in the air decreases to a level lower than the critical concentration by ventilation or the like, the organic solvent vapor adsorbed by the adsorbent is quickly desorbed. Therefore, the adsorbent continuously retains the ability as an adsorbent without any special regeneration treatment such as heat treatment or the like. This is a very advantageous feature when compared with the conventional adsorbent utilizing active carbon, zeolite or the like, for which a regeneration treatment such as heat treatment is required when the adsorption continued. Further, when the vapor of the organic solvent is lower than the critical concentration, adsorption of the vapor scarcely occurs, so that adsorbent is free from deterioration of the adsorption ability due to accumulation of the vapor of the organic solvent. Therefore, the adsorbent according to the present invention may be used permanently keeping its ability.

As for the mode of use of the adsorbent of volatile organic compounds according to the present invention, the molecular crystals, preferably single crystals of the organic carboxylic acid metal complex may be placed in a vessel having air vents and the vessel may be left in a room or the like. Alternatively, the adsorbent may be blended as an adsorbent component in a composition such as paint or building material, which generates organic solvent vapor. Still alternatively, the adsorbent according to the present invention may be packed in air-permeable sacks or the like, and the sacks may be embedded in the walls, under the floor or the like. The term "placing in the air the adsorbent of volatile organic compounds" as used in the present description and claims includes any of these modes.

The volatile organic compounds to be adsorbed by the adsorbent of volatile organic compounds according to the present invention herein means organic compounds whose vapor is diffused at normal temperature from the organic compound which is in liquid state at normal temperature or from the solution of the organic compound, which solution is in liquid state at normal temperature. The organic compound is not restricted as long as it is volatile, and vapors of organic solvents and vapors of aldehydes such as formaldehyde are preferred. Although the organic solvents are not restricted, preferred examples thereof include aliphatic organic solvents such as alkanes, e.g., hexane, heptane and octane, and derivatives (halogenated products and the like) thereof; and aromatic organic solvents such as benzene, toluene and xylene. Since these organic solvents and aldehydes are a part of the causal substances of sick house, the adsorbent of the present invention is useful for the prevention of sick house. Although formaldehyde is in the form of gas at normal temperature, since concentrated aqueous solutions and formalin which are in liquid form at normal temperature are widely used, and since formaldehyde is vaporized from these solutions at normal temperature, it is included in "volatile organic compound" as used in the present invention.

Although the critical concentration differs depending on the type of the organic carboxylic acid metal complex used and on the type of the organic solvent, it is usually about 1 mmHg to 10 mmHg. Since the critical concentration is the concentration of the organic solvent vapor in the air which the adsorbent of the present invention contacts, in cases where the adsorbent of the present invention is blended in the paint or building material, or even in cases where it is used independently as an adsorbent, when it is placed in the vicinity of a wall or floor which generates the organic solvent vapor, the concentration of the organic solvent vapor at the site is maintained at the critical concentration or less. Therefore, the concentration of the organic solvent vapor in the air apart from the wall or floor can be maintained at a level lower than the critical concentration.

The above-described organic carboxylic acid metal complex easily adsorbs and easily desorbs hydrogen, and the diffusion of the hydrogen is quick, so that absorption equilibrium is reached in a short time. As will be concretely shown in the Examples below, the crystal structure of the organic carboxylic acid metal complex realizes a stable adsorbed structure of hydrogen, and associated hydrogen is generated at a high density in the microvoids in the crystal. Therefore, the organic carboxylic acid metal complex can be advantageously used as a hydrogen-absorbing material.

The hydrogen-absorbing material according to the present invention can be used in the same manner as the conventional hydrogen-absorbing materials made of alloys. For example, the hydrogen-absorbing material of the present invention may be packed in a tightly closed vessel, and hydrogen gas may be made to be absorbed at a high pressure. When using the hydrogen gas, the hydrogen gas may be taken out of the vessel and used. The taken out hydrogen gas may be utilized as a fuel of hydrogen engine or the like.

By making the crystal of above-described organic carboxylic acid metal complex adsorb metal vapor, the metal atoms are aligned one-dimensionally in a single line. Such a line made of the metal atoms is theoretically the thinnest metal line. Since the metal atoms are arranged in a distance at which flowing of free electrons occurs, electric current can pass therethrough. Therefore, such a metal line can be used as the thinnest wiring, and is useful as microwirings of the quantum semiconductors and various nanotech devices which are now being developed.

As described above, the present invention further provides an organic carboxylic acid metal complex per se constituted by recurring units of the above-described Formula [I] (wherein in Formula [I], $M^1$ and $M^2$; $R^{1a}$, $R^{1b}$, $R^{1c}$ and $R^{1d}$; and $R^2$, $R^3$, $R^4$ and $R^5$ have the same meanings as described above, with the proviso that $R^2$, $R^3$, $R^4$ and $R^5$ are not simultaneously hydrogen atoms). These organic carboxylic acid metal complexes per se are novel substances. As the explanations about $M^1$ and $M^2$; $R^{1a}$, $R^{1b}$, $R^{1c}$ and $R^{1d}$; and $R^2$, $R^3$, $R^4$ and $R^5$ in Formula [I] and preferred examples thereof, the above-described explanations and preferred examples are equally applied as they are (with the proviso that $R^2$, $R^3$, $R^4$ and $R^5$ are not simultaneously hydrogen atoms). The number of the recurring units represented by Formula [I] is not restricted, and usually 10 to $10^8$, preferably about $10^2$ to $10^7$. However, in cases where the organic carboxylic acid metal complex represented by Formula [I] is in the form of the large single crystal produced by the method according to the present first invention, the number of the recurring units is usually $10^7$ to $10^{10}$, preferably about $8 \times 10^7$ to 109 as described above.

The present invention further provides single crystalline organic carboxylic acid metal complex constituted by recurring units of the Formula [I] (wherein in Formula [I], $M^1$ and $M^2$; $R^{1a}$, $R^{1b}$, $R^{1c}$ and $R^{1d}$; and $R^2$, $R^3$, $R^4$ and $R^5$ have the same meanings as described above), which single crystal has a longer side not shorter than 1 μm. The crystals having a crystal system of monoclinic system and a space group of C2/c, or having a crystal system of triclinic system and a space group of P-1 are preferred (see Examples below).

The organic carboxylic acid metal complex forms a molecular crystal, and in the molecular crystal, one-dimensionally extending voids (channel structures) or regularly arranged spaces exist. In the intracrystal spaces, gas molecules can be adsorbed and desorbed as guests. Since gas molecules can be adsorbed to and desorbed from the intracrystal spaces, the organic carboxylic acid metal complex according to the present invention can be used as a gas adsorbent. The gas adsorbent can be used for storage or separation and concentration of gases. The organic carboxylic acid metal complex according to the present invention changes the crystal structure upon clathrating the gas molecules, and the shape and size of the channel structure are changed. Therefore, it can optimally clathrate various gas molecules, and the amount of absorbed gas per a unit volume is large. Further, since the single crystal of the organic carboxylic acid metal complex according to the present invention is a porous body having channel structures therein, it can be used as a gas adsorption film as it is. The gas adsorption film can be used as a filter for separation and concentration of gases or the like.

EXAMPLES

The present invention will now be described by way of examples thereof. However, the present invention is not restricted to the Examples below.

Example 1

Synthesis of Single Crystals of Cupric (II) Benzoate Pyrazine Adduct

Cupric (II) acetate monohydrate in an amount of 350 mg (3.50 mmol) and 50-fold amount, that is, 21.4 g (176 mmol) of benzoic acid were dissolved in 350 ml of methanol, and the resulting solution was poured to 50 ml of Florinate (trade name, produced by 3M, FC77) in a Teflon (registered trademark)-coated vessel. In the condition where the mixture was separated into two layers wherein the upper layer was constituted by the methanol solution and the lower layer was constituted by Florinate (trade name), pyrazine dissolved in ethylene glycol so as to reduce the vapor pressure was introduced into the solution by vapor diffusion, and allowed to react at 20° C. The vapor diffusion was carried out by carefully holding a test tube containing the pyrazine solution in ethylene glycol such that the test tube does not contact the reaction solution, and allowing the pyrazine vapor to slowly dissolved into the reaction solution. Crystals were grown at the interface between the Florinate-methanol layers. One month later, the desired products were isolated as single crystals by filtration, and dried in the air to obtain 360 mg of blue plate-like single crystals (yield: 60%). Calculating from the sizes of the crystals (about $10^7$ per 1 cm of crystal), the number of repeating units was about $5\times10^6$ to $10^7$.

Example 2

Synthesis of Single Crystals of Rhodium (II) Benzoate Pyrazine Adduct

In 40 ml of acetonitrile, 20 mg (3.50 mmol) of rhodium (H) benzoate was dissolved, and the resulting solution was poured to 5 ml of Florinate (trade name, produced by 3M, FC77) in a Teflon (registered trademark)-coated vessel. In the condition where the mixture was separated into two layers wherein the upper layer was constituted by the acetonitrile solution and the lower layer was constituted by Florinate (trade name), pyrazine dissolved in ethylene glycol so as to reduce the vapor pressure was introduced into the solution by vapor diffusion in the same manner as in Example 1, and allowed to slowly react at 15° C. Crystals were grown at the interface between the Florinate-methanol layers. One month later, the desired products were isolated as single crystals by filtration to obtain 360 mg of red plate-like single crystals (yield: 70%). Calculating from the sizes of the crystals produced, the number of repeating units was about $10^6$ to $7\times10^6$.

Figure 2:
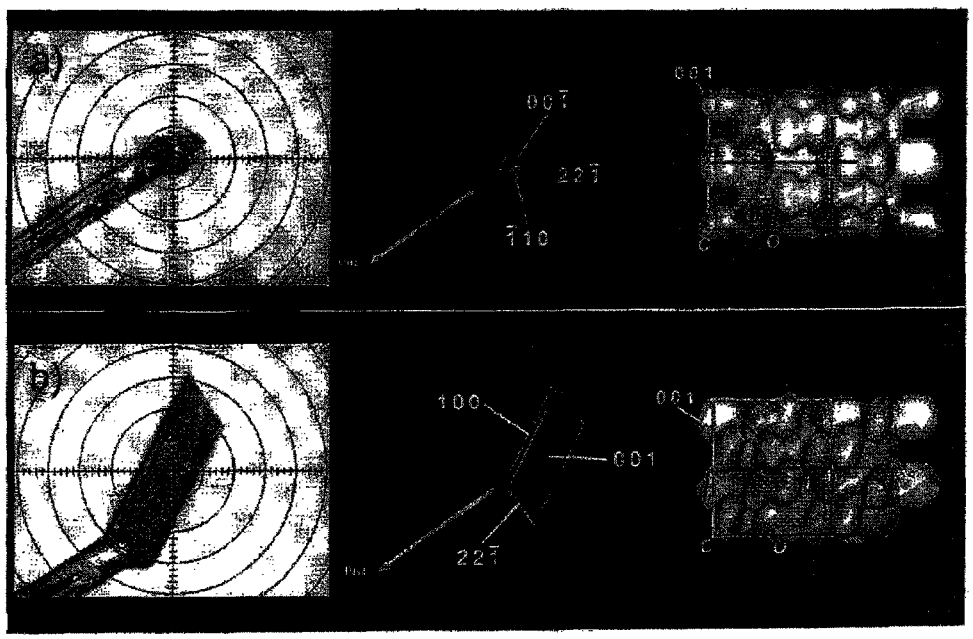
FIG. 2 are schematic views of the stereoscopic micrographs of the large single crystals obtained in Examples 1 and 2, as well as the indices of crystal plane and positional relationship between the crystal faces and the direction of the channel, revealed by X-ray analysis of the structures of the single crystals.
Figure 3:
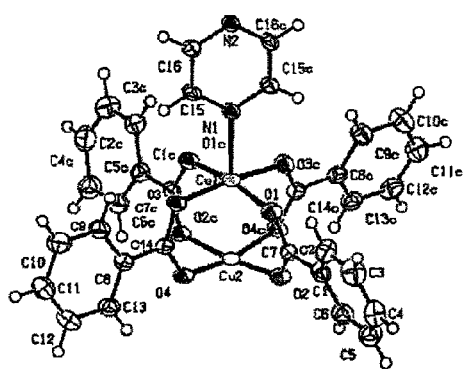
FIG. 3 shows the results of the X-ray analysis of the structure of the large single crystal obtained in Example 1.
Figure 4:
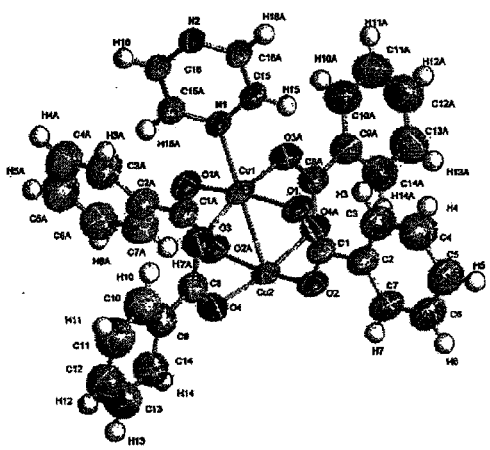
FIG. 4 shows the results of the X-ray analysis of the structure of the large single crystal obtained in Example 2.
Figure 5:
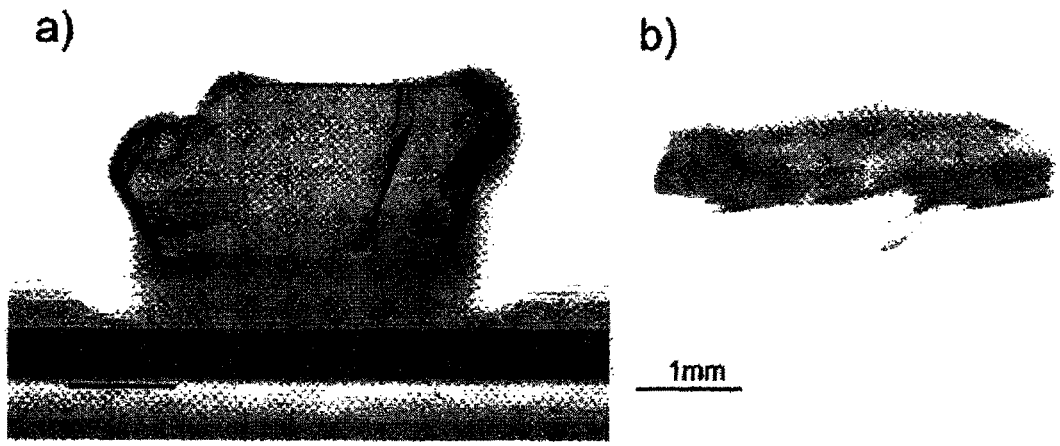
FIG. 5 shows the stereoscopic micrograph (a) and an X-ray topography (b) of the large single crystal obtained in Example 1.

Schematic views of the stereoscopic micrographs of the large single crystals obtained in Examples 1 and 2 are shown in FIG. 1. The left view in FIG. 1 is a schematic view of a photograph of the single crystals obtained in Example 1, and the right view is a schematic view of a photograph of the single crystals obtained in Example 2. Schematic views of the stereoscopic micrographs of the large single crystals obtained in Examples 1 and 2, as well as the indices of crystal plane and positional relationship between the crystal faces and the direction of the channel, revealed by X-ray analysis of the structures of the single crystals, are shown in FIG. 2. In FIG. 2, a) shows the results about the single crystals obtained in Example 1, and b) shows the results about the single crystals obtained in Example 2. Results of the X-ray analysis of the structures of the single crystals are shown in FIGS. 3 and 4, respectively. Further, a schematic view (a) in FIG. 5) of the stereoscopic micrograph and a schematic view (b) in FIG. 5) of the X-ray topograph of the large single crystal obtained in Example 1 are shown in FIG. 5.

Examples 3 to 8

Production of Copper Complexes and Physical Properties

In 80 ml of methanol, 80 mg ($2.4\times10^4$ mol) of cupric (II) acetate monohydrate and 117.2 mg ($8.4\times10^{-4}$ mol) of benzoic acid were dissolved to obtain a blue solution. After filtration, 8.0 mg of pyrazine (Example 3), 0.3 ml of 2-methylpyrazine (Example 4), 0.3 ml of 2,3-dimethylpyrazine (Example 5), 0.3 ml of 2-ethylpyrazine (Example 6), 0.3 ml of 2,3-diethylpyrazine (Example 7) or 0.3 ml of 2-propylpyrazine (Example 8) was added thereto, and the resulting mixture was allowed to react slowly at room temperature for 24 hours. Blue single crystals were generated. Pyrazine complex (Example 3): 12.2 mg (58.6%), 2-methylpyrazine complex (Example 4): 11.7 mg (57.4%), 2,3-dimethylpyrazine complex (Example 5): 16.0 mg (74.2%), 2-ethylpyrazine complex (Example 6) (19.2%), 2,3-diethylpyrazine complex (Example 7) (13.2%), 2-propylpyrazine complex (Example 8) (39.3%). Identification was carried out by X-ray structure analysis of the single crystals and elementary analysis. Calculating from the sizes of the crystals (about $10^7$ per 1 cm of crystal), the number of repeating units was about $10^4$ to $4\times10^5$.

The results of the elementary analysis and X-ray structure analysis are shown in Table 1 below.

TABLE 1

Figure 23:
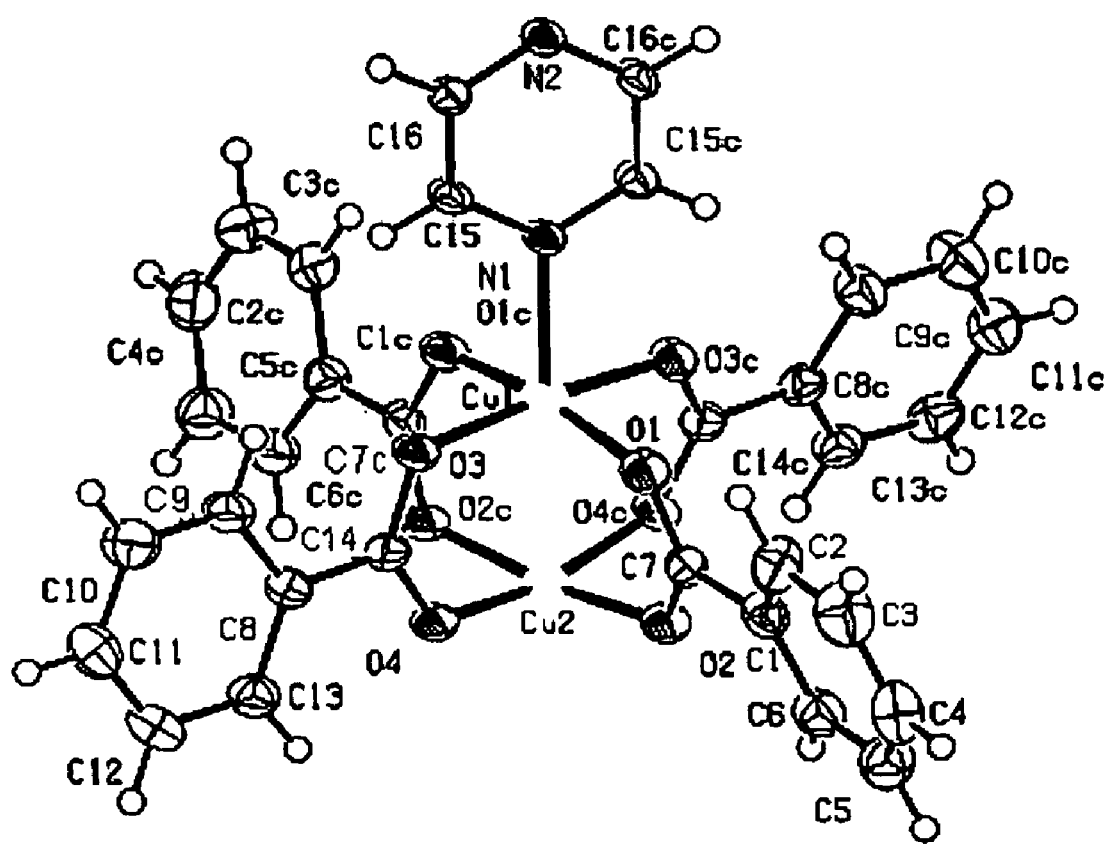
FIG. 23 shows the results of the X-ray analysis of the structure of the large single crystal obtained in Example 3.
Figure 24:
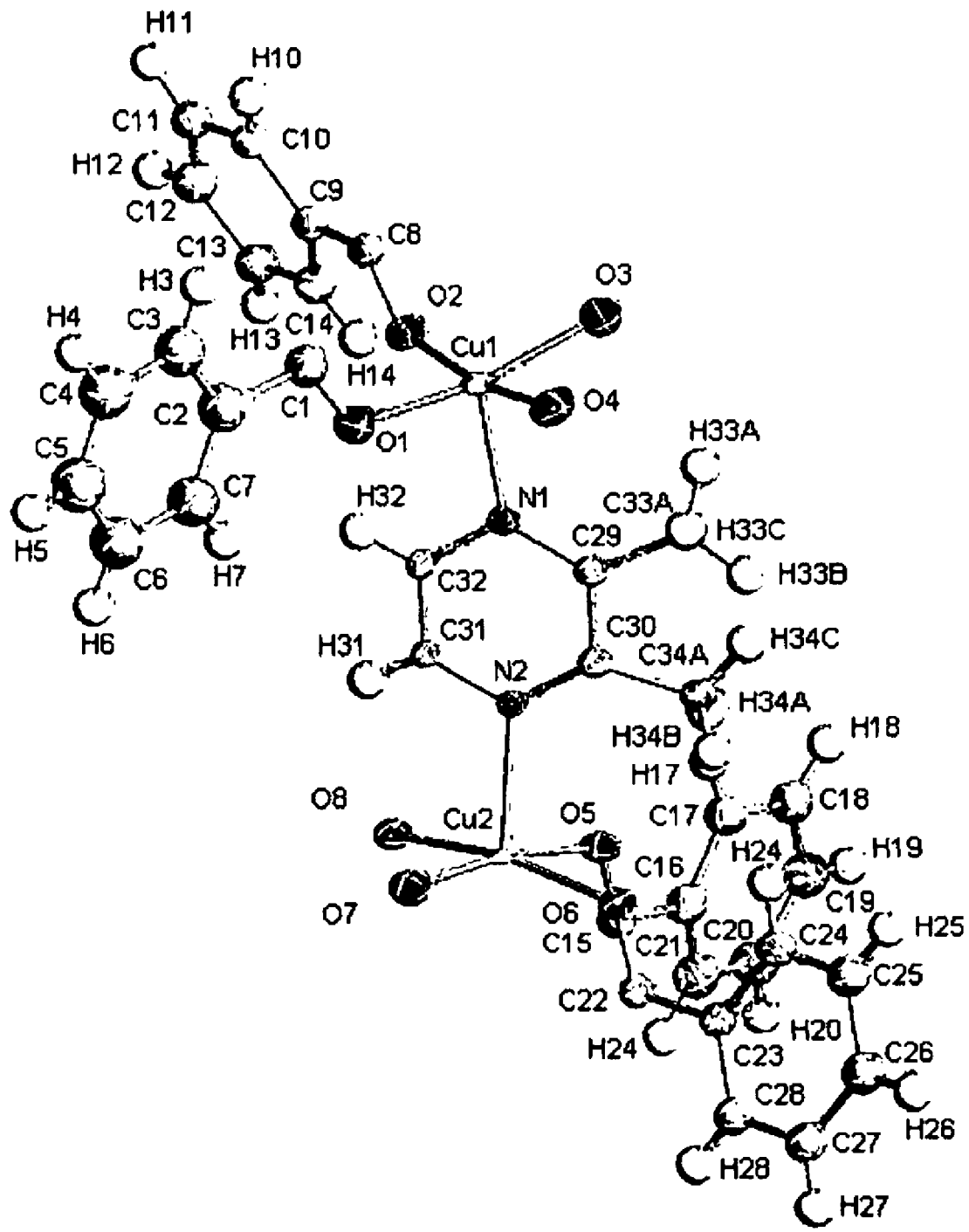
FIG. 24 shows the results of the X-ray analysis of the structure of the large single crystal obtained in Example 4.
Figure 25:
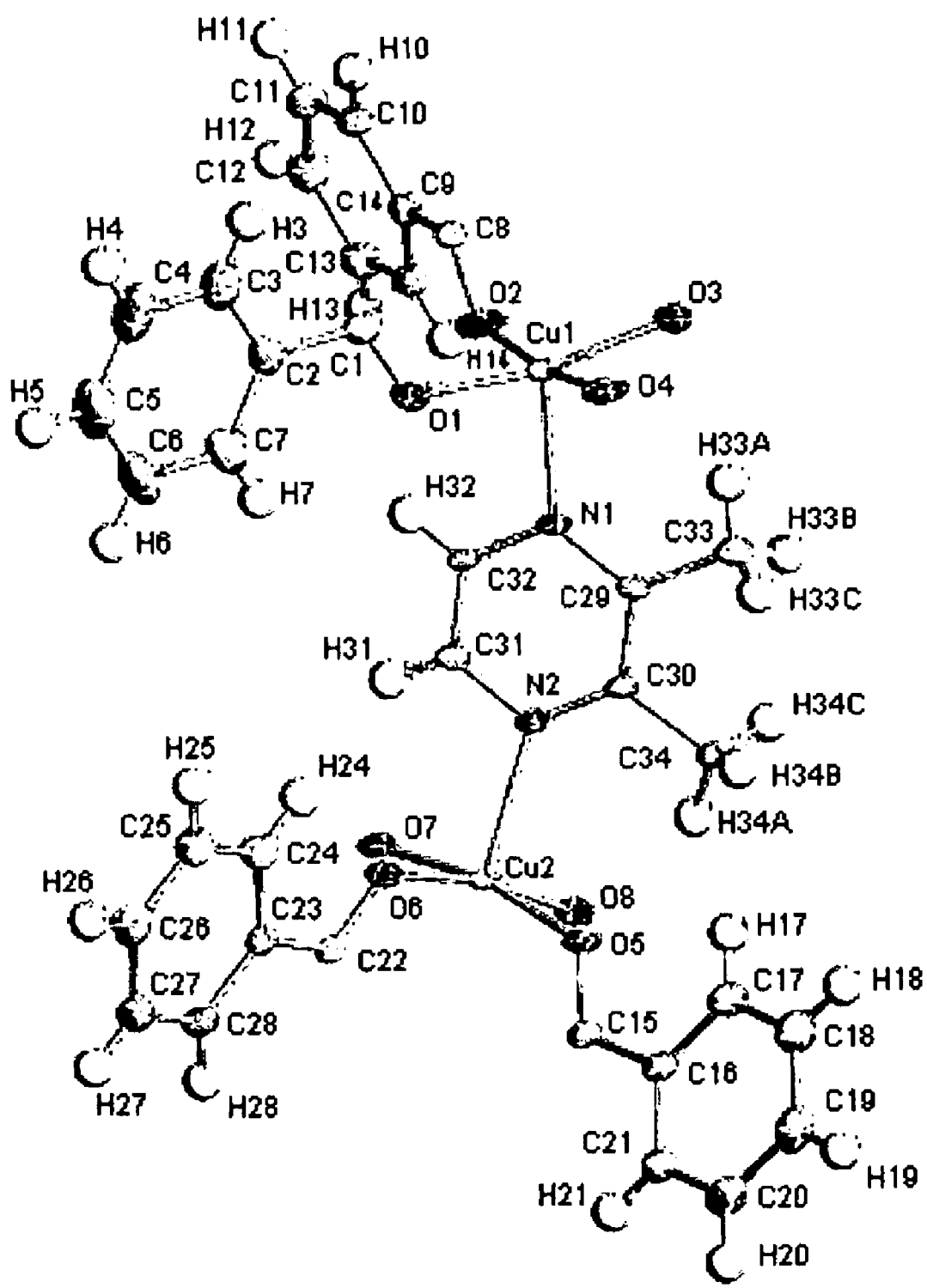
FIG. 25 shows the results of the X-ray analysis of the structure of the large single crystal obtained in Example 5.
Figure 26:
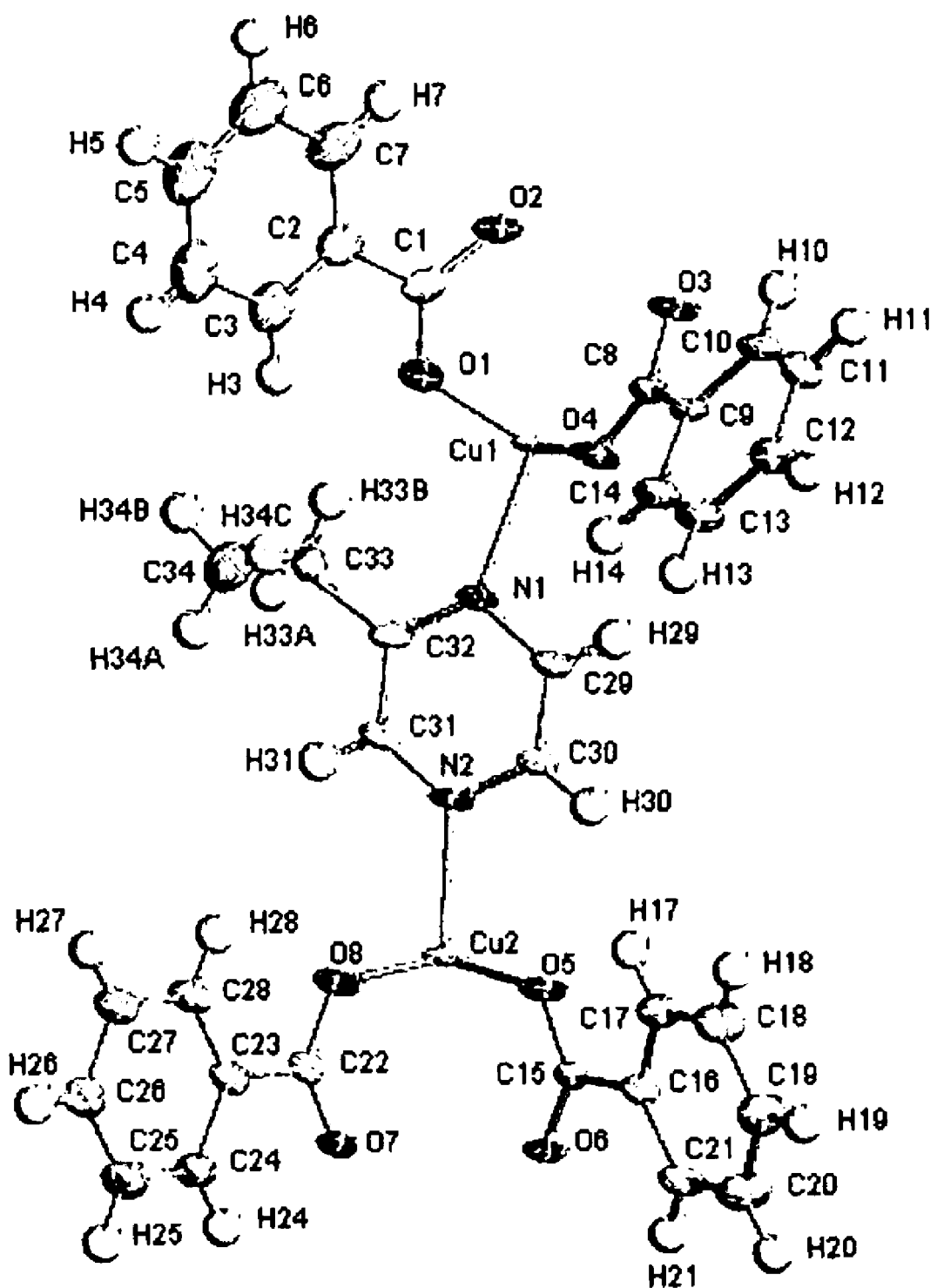
FIG. 26 shows the results of the X-ray analysis of the structure of the large single crystal obtained in Example 6.
Figure 27:
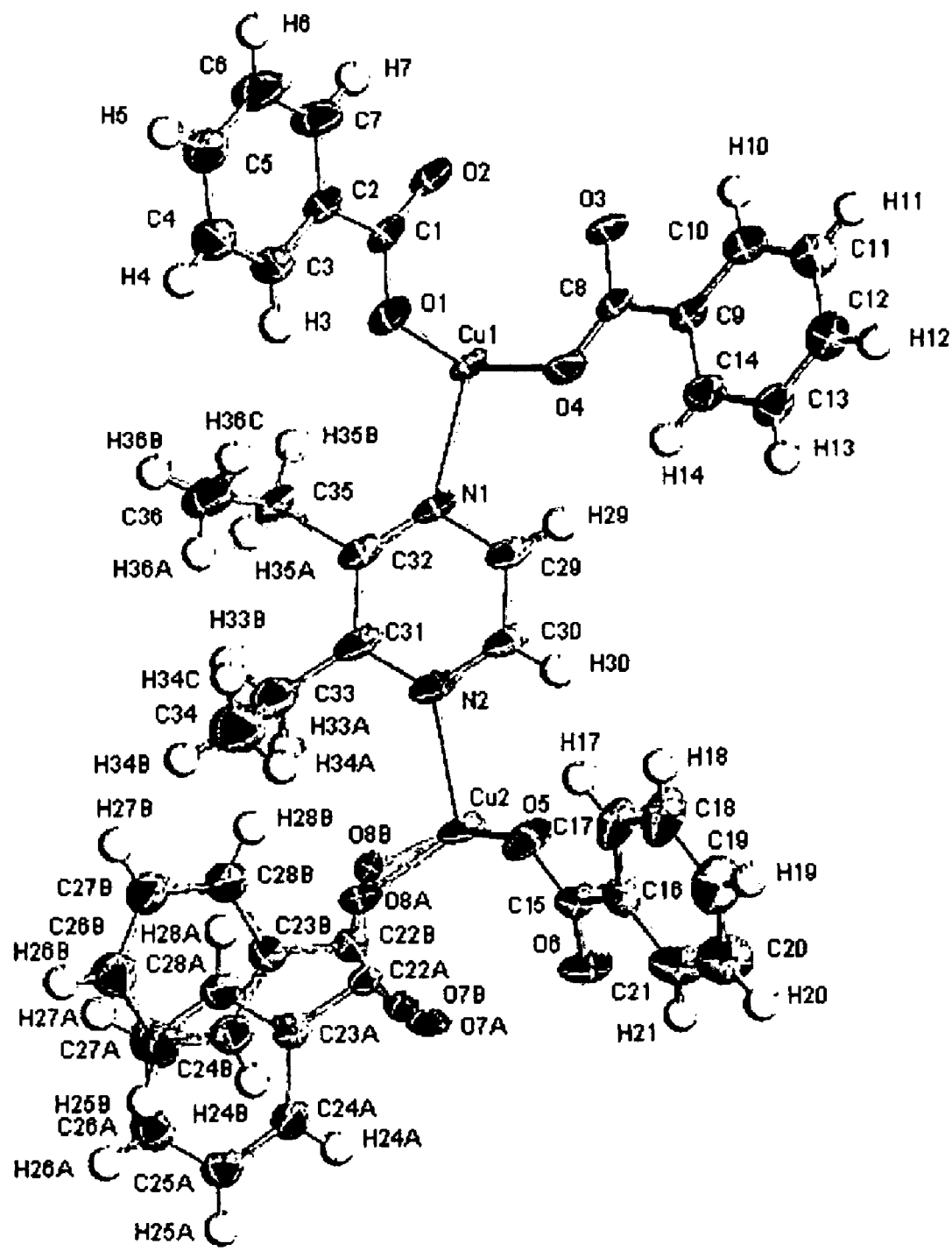
FIG. 27 shows the results of the X-ray analysis of the structure of the large single crystal obtained in Example 7.
Figure 28:
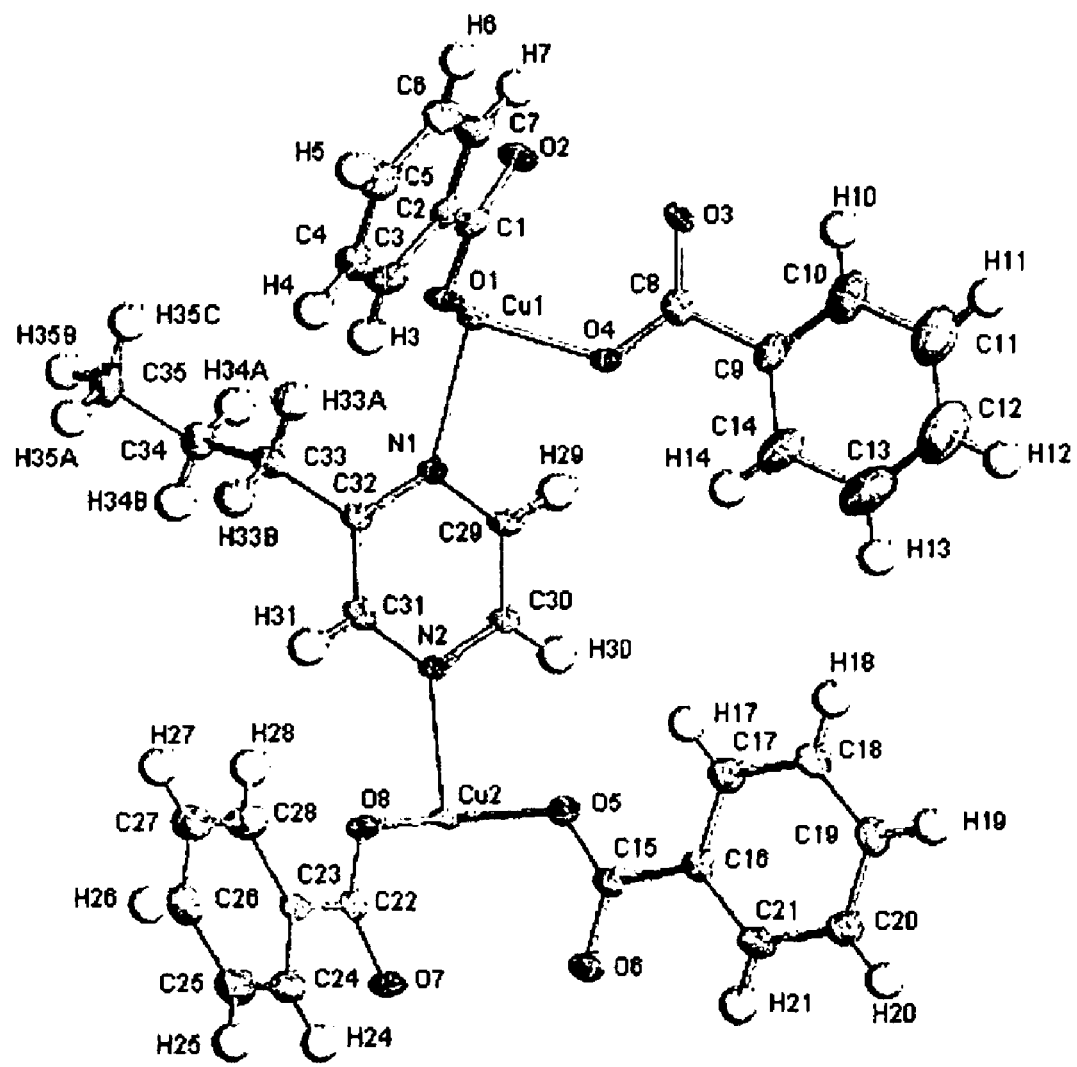
FIG. 28 shows the results of the X-ray analysis of the structure of the large single crystal obtained in Example 8.

| Example | Elementary Analysis Data | X-ray Structure Analysis Data |
|---|---|---|
| Example 3 | Anal. Calcd. for $C_{32}H_{24}Cu_2N_2O_8$: C, 55.57; H, 3.50; N, 4.05%. Found: C, 54.43; H, 3.44; N, 4.17%. | See FIG. 23 |
| Example 4 | Anal. Calcd. for $C_{33}H_{26}Cu_2N_2O_8$: C, 56.17; H, 3.71; N, 3.97%. Found: C, 55.19; H, 3.62; N, 4.09%. | See FIG. 24 |
| Example 5 | Anal. Calcd. for $C_{34}H_{28}Cu_2N_2O_8$: C, 56.74; H, 3.92; N, 3.89%. Found: C, 55.70; H, 3.86; N, 4.01%. | See FIG. 25 |
| Example 6 | Anal. Calcd. for $C_{34}H_{28}N_2O_8Cu_2$: C, 56.74; H, 3.92; N, 3.89%. Found: C, 55.90; H, 3.88; N, 4.07%. | See FIG. 26 |
| Example 7 | Anal. Calcd. for $C_{36}H_{32}N_2O_8Cu_2$: C, 57.29; H, 4.31; N, 3.75%. Found: C, 56.75; H, 4.32; N, 3.86%. | See FIG. 27 |
| Example 8 | Anal. Calcd. for $C_{35}H_{30}N_2O_8Cu_2$: C, 57.29; H, 4.12; N, 3.82%. Found: C, 56.91; H, 4.10; N, 4.05%. | See FIG. 28 |

The physical data of the respective obtained single crystals are summarized in Tables 2-1 and 2-2 below.

TABLE 2-1

|  | Example 3 | Example 4 | Example 5 |
|---|---|---|---|
| Composition Formula | $C_{32}H_{24}N_2O_8Cu_2$ | $C_{33}H_{26}N_2O_8Cu_2$ | $C_{34}H_{28}N_2O_8Cu_2$ |
| Molecular Weight | 691.64 | 704.63 | 719.66 |
| Measuring Temperature [K] | 298 | 90 | 90 |
| Crystal System | monoclinic system | triclinic system | triclinic system |
| Space Group | C2/c | P-1 | P-1 |
| a [Å] | 18.070 (8) | 10.213 (4) | 10.2611 (6) |
| b [Å] | 9.700 (4) | 10.386 (4) | 10.4184 (6) |
| c [Å] | 18.968 (8) | 15.673 (6) | 15.6335 (9) |
| α [degree] | 90 | 80.728 (8) | 81.1410 (10) |
| β [degree] | 97.564 (11) | 82.581 (8) | 82.3020 (10) |
| γ [degree] | 90 | 86.601 (8) | 87.7220 (10) |
| Volume [Å³] | 3296 (2) | 1625.8 (11) | 1636.16 (16) |
| Z | 4 | 2 | 2 |
| Density (Calcd.) [Mg/m³] | 1.394 | 1.439 | 1.461 |
| Crystal Size [mm] | 0.45 × 0.10 × 0.04 | 0.22 × 0.08 × 0.04 | 0.30 × 0.08 × 0.04 |

TABLE 2-2

|  | Example 6 | Example 7 | Example 8 |
|---|---|---|---|
| Composition Formula | $C_{34}H_{28}N_2O_8Cu_2$ | $C_{36}H_{32}N_2O_8Cu_2$ | $C_{35}H_{30}N_2O_8Cu_2$ |
| Molecular Weight | 719.66 | 747.72 | 733.69 |
| Measuring Temperature [K] | 90 | 90 | 90 |
| Crystal System | triclinic system | triclinic system | triclinic system |
| Space Group | P-1 | P-1 | P-1 |
| a [Å] | 10.291 (2) | 10.375 (2) | 10.2767 (9) |
| b [Å] | 10.410 (2) | 10.419 (2) | 10.6404 (9) |
| c [Å] | 15.511 (3) | 15.850 (4) | 15.4597 (13) |
| α [degree] | 80.375 (4) | 101.079 (5) | 99.099 (2) |
| β [degree] | 82.201 (4) | 93.722 (5) | 96.733 (2) |
| γ [degree] | 86.782 (5) | 94.320 (5) | 90.448 (2) |
| Volume [Å³] | 1622.2 (6) | 1671.2 (6) | 1657.1 (2) |
| Z | 2 | 2 | 2 |
| Density (Calcd.) [Mg/m³] | 1.473 | 1.486 | 1.470 |
| Crystal Size [mm] | 0.34 × 0.20 × 0.15 | 0.43 × 0.24 × 0.01 | 0.21 × 0.21 × 0.02 |

Examples 9-14

Production of Rhodium Complex and Physical Properties

In 80 ml of acetonitrile, 80 mg ($1.0 \times 10^{-4}$ mol) of synthesized rhodium benzoate was dissolved to obtain a reddish purple solution. After filtration, 8.0 mg of pyrazine (Example 9), 0.3 ml of 2-methylpyrazine (Example 10), 0.3 ml of 2,3-dimethylpyrazine (Example 11), 0.3 ml of 2-ethylpyrazine (Example 12), 0.3 ml of 2,3-diethylpyrazine (Example 13) or 0.3 ml of 2-propylpyrazine (Example 14) was added, and the resulting mixture was allowed to react slowly at room temperature. Brown microcrystals were generated. pyrazine complex (Example 7): 12.9 mg (67.2%), 2-methylpyrazine complex (Example 8): 11.9 mg (60.7%), 2,3-dimethylpyrazine complex (Example 9): 16.3 mg (81.7%), 2-ethylpyrazine complex (Example 10) (42.6%), 2,3-diethylpyrazine complex (Example 11) (85.5%), 2-propylpyrazine complex (Example 12) (14.6%). Identification was carried out by X-ray structure analysis of the single crystals and elementary analysis. Calculating from the sizes of the crystals (about $10^7$ per 1 cm of crystal), the number of repeating units each represented by Formula [I] was about $10^4$ to $5 \times 10^5$.

Results of elementary analysis and the results of X-ray structure analysis are shown in Table 3 below.

TABLE 3

Figure 29:
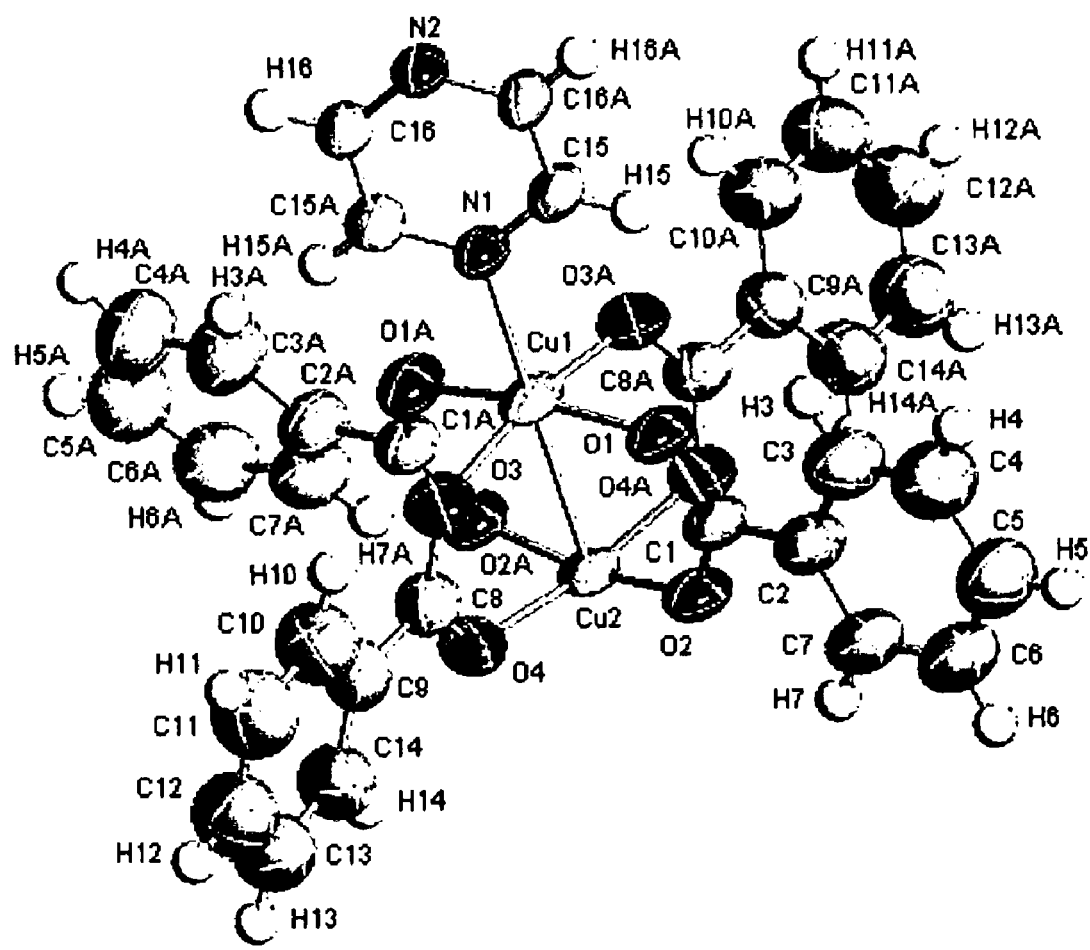
FIG. 29 shows the results of the X-ray analysis of the structure of the large single crystal obtained in Example 9.
Figure 30:
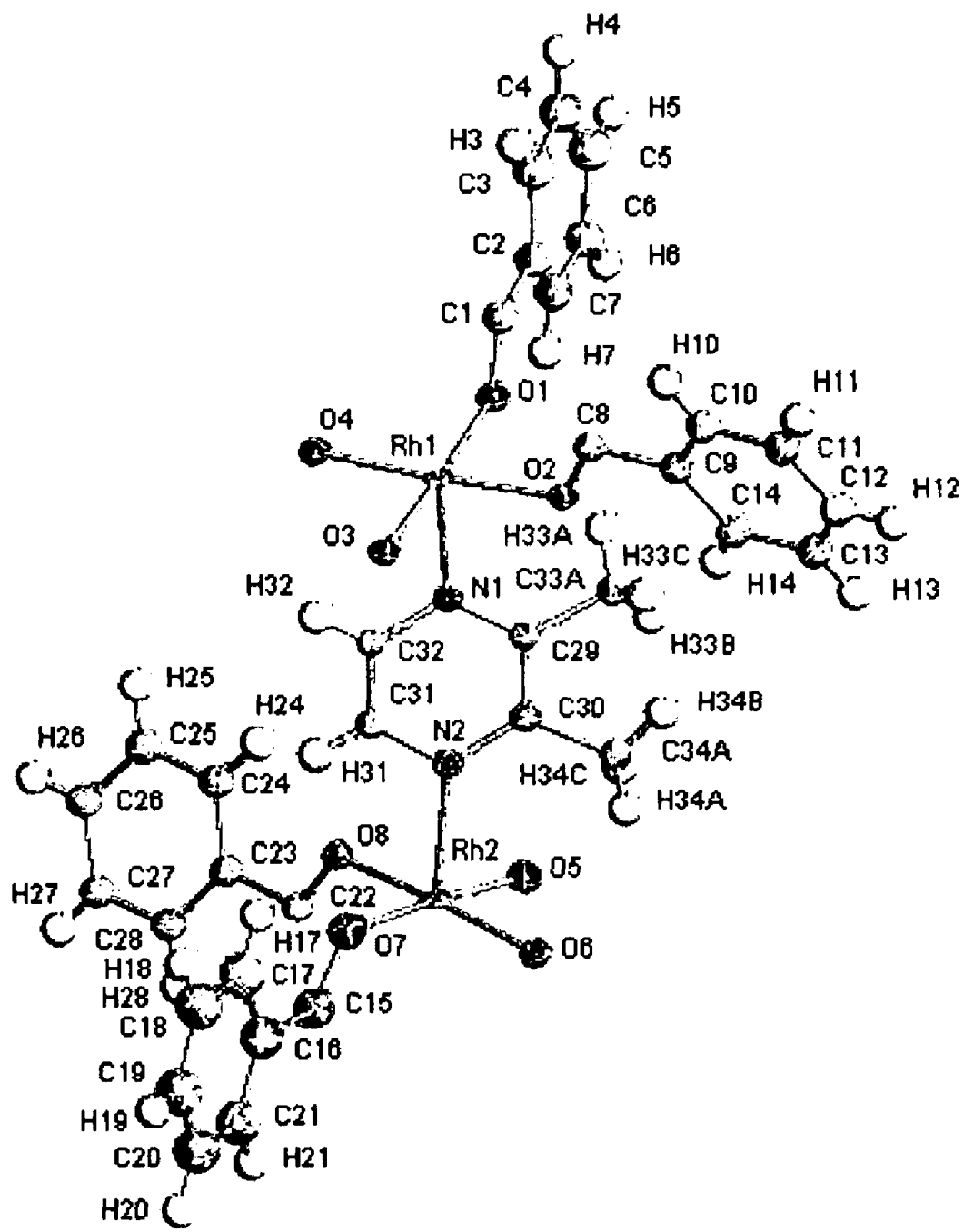
FIG. 30 shows the results of the X-ray analysis of the structure of the large single crystal obtained in Example 10.
Figure 31:
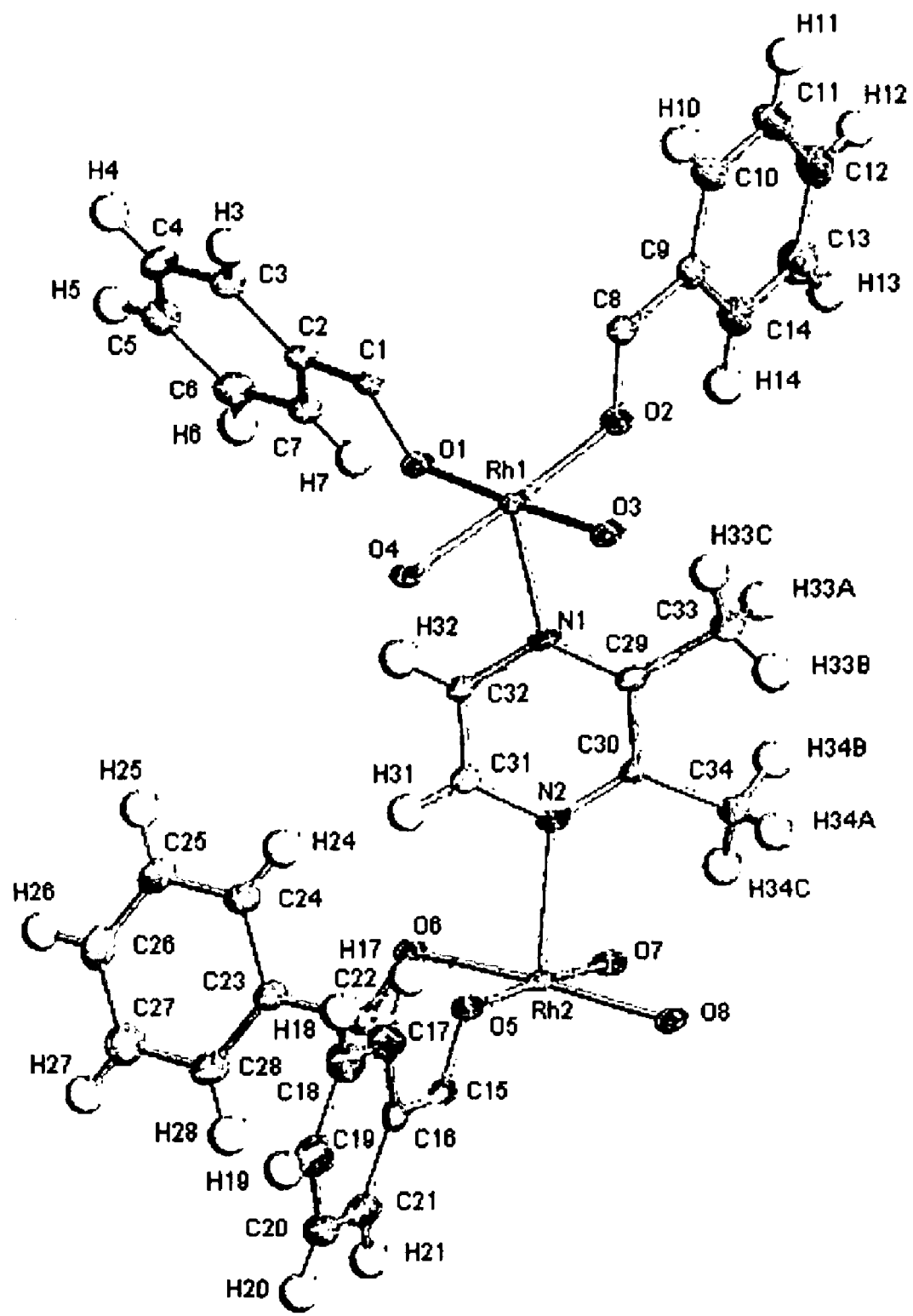
FIG. 31 shows the results of the X-ray analysis of the structure of the large single crystal obtained in Example 11.
Figure 32:
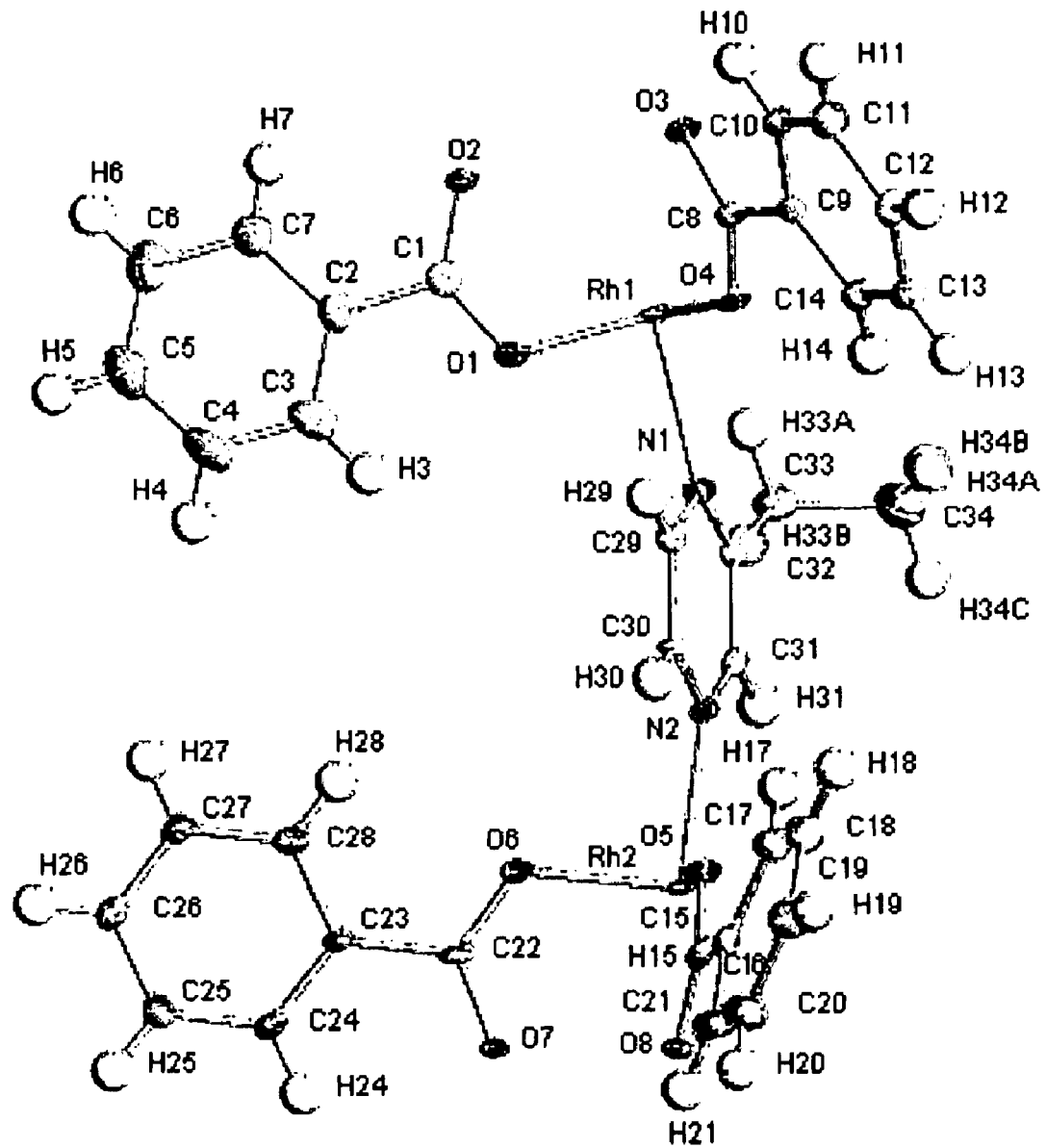
FIG. 32 shows the results of the X-ray analysis of the structure of the large single crystal obtained in Example 12.
Figure 33:
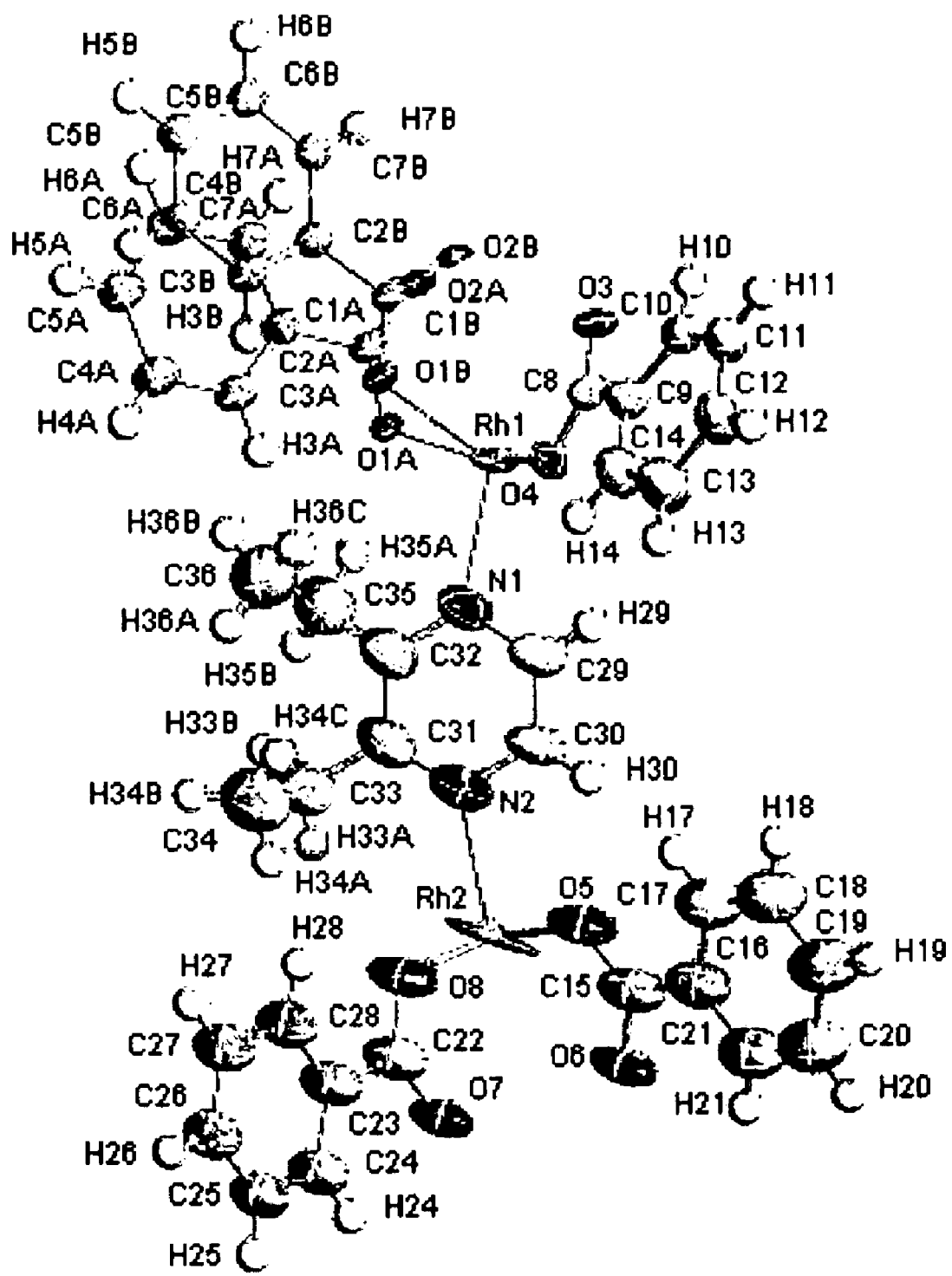
FIG. 33 shows the results of the X-ray analysis of the structure of the large single crystal obtained in Example 13.
Figure 34:
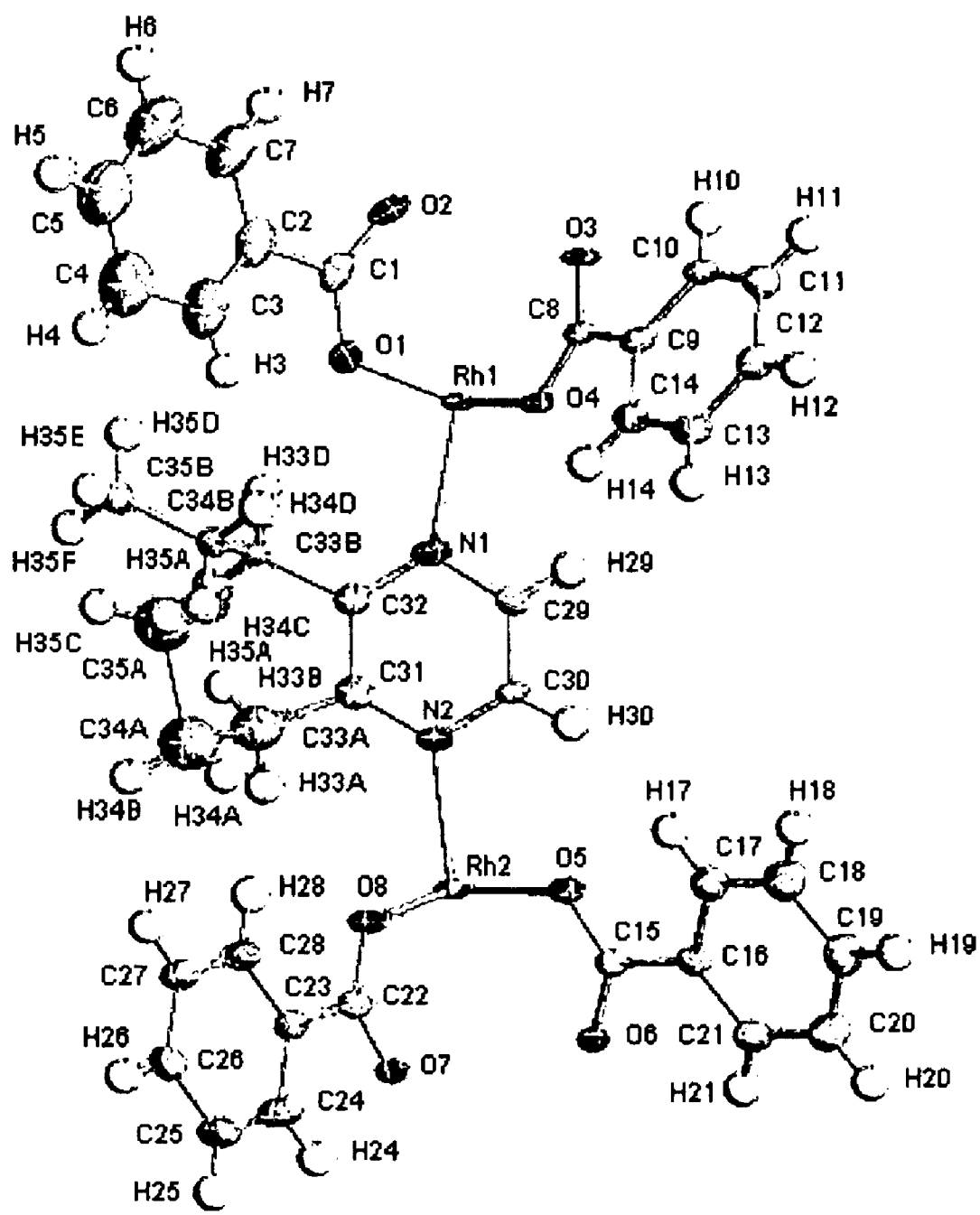
FIG. 34 shows the results of the X-ray analysis of the structure of the large single crystal obtained in Example 14.

| Example | Elementary Analysis Data | X-ray Structure Analysis Data |
|---|---|---|
| Example 9 | Anal. Calcd. for $C_{32}H_{24}Rh_2N_2O_8$: C, 49.89; H, 3.14; N, 3.64%. Found: C, 49.53; H, 3.18; N, 3.72%. | See FIG. 29 |
| Example 10 | Anal. Calcd. for $C_{33}H_{26}Rh_2N_2O_8$: C, 50.53; H, 3.34; N, 3.57%. Found: C, 49.99; H, 3.31; N, 3.62%. | See FIG. 30 |
| Example 11 | Anal. Calcd. for $C_{34}H_{28}Rh_2N_2O_8$: C, 51.15; H, 3.54; N, 3.51%. Found: C, 50.23; H, 3.55; N, 3.40%. | See FIG. 31 |
| Example 12 | Anal. Calcd. for $C_{34}H_{28}N_2O_8Rh_2$: C, 51.15; H, 3.53; N, 3.51%. Found: C, 50.95; H, 3.41; N, 3.69%. | See FIG. 32 |
| Example 13 | Anal. Calcd. for $C_{36}H_{32}N_2O_8Rh_2$: C, 52.32; H, 3.53; N, 3.39%. Found: C, 52.13; H, 3.84; N, 3.46%. | See FIG. 33 |
| Example 14 | Anal. Calcd. for $C_{35}H_{30}N_2O_8Rh_2$: C, 51.74; H, 3.72; N, 3.45%. Found: C, 51.57; H, 3.78; N, 3.51%. | See FIG. 34 |

The physical data of the respective obtained single crystals are summarized in Tables 4-1 and 4-2 below.

TABLE 4-1

|  | Example 9 | Example 10 | Example 11 |
|---|---|---|---|
| Composition Formula | $C_{32}H_{24}N_2O_8Rh_2$ | $C_{33}H_{26}N_2O_8Rh_2$ | $C_{34}H_{28}N_2O_8Rh_2$ |
| Molecular Weight | 770.36 | 783.37 | 798.40 |
| Measuring Temperature [K] | 293 | 90 | 90 |
| Crystal System | monoclinic system | triclinic system | triclinic system |
| Space Group | C2/m | P-1 | P-1 |
| a [Å] | 17.821 (9) | 10.2076 (9) | 10.2633 (5) |
| b [Å] | 9.605 (5) | 10.4184 (10) | 10.4611 (5) |
| c [Å] | 12.362 (8) | 15.7516 (15) | 15.7171 (7) |
| α [degree] | 90 | 79.434 (2) | 79.8530 (10) |

TABLE 4-1-continued

|  | Example 9 | Example 10 | Example 11 |
|---|---|---|---|
| β [degree] | 127.53 (4) | 81.217 (2) | 81.0400 (10) |
| γ [degree] | 90 | 86.212 (2) | 87.3630 (10) |
| Volume [Å$^3$] | 1678 (1) | 1626.2 (3) | 1640.51 (13) |
| Z | 2 | 2 | 2 |
| Density (Calcd.) [Mg/m$^3$] | 1.524 | 1.600 | 1.616 |
| Crystal Size [mm] | 0.10 × 0.08 × 0.02 | 0.16 × 0.10 × 0.04 | 0.30 × 0.14 × 0.01 |

TABLE 4-2

|  | Example 12 | Example 13 | Example 14 |
|---|---|---|---|
| Composition Formula | $C_{34}H_{28}N_2O_8Rh_2$ | $C_{36}H_{32}N_2O_8Rh_2$ | $C_{35}H_{30}N_2O_8Rh_2$ |
| Molecular Weight | 798.40 | 826.46 | 811.42 |
| Measuring Temperature [K] | 90 | 90 | 90 |
| Crystal System | triclinic system | triclinic system | triclinic system |
| Space Group | P-1 | P-1 | P-1 |
| a [Å] | 10.2833 (10) | 10.4455 (13) | 10.3793 (8) |
| b [Å] | 10.4707 (10) | 10.5151 (12) | 10.5963 (9) |
| c [Å] | 15.5700 (15) | 15.757 (2) | 15.5510 (13) |
| α [degree] | 79.133 (2) | 95.787 (3) | 100.008 (2) |
| β [degree] | 81.323 (2) | 100.565 (3) | 97.602 (2) |
| γ [degree] | 86.287 (2) | 93.873 (3) | 90.186 (2) |
| Volume [Å$^3$] | 1626.4 (3) | 1686.1 (4) | 1668.9 (2) |
| Z | 2 | 2 | 2 |
| Density (Calcd.) [Mg/m$^3$] | 1.630 | 1.628 | 1.615 |
| Crystal Size [mm] | 0.22 × 0.14 × 0.01 | 0.34 × 0.16 × 0.01 | 0.20 × 0.12 × 0.02 |

Example 15

Adsorption and Desorption of Organic Solvent Vapor

Each of the organic carboxylic acid metal complexes produced in Examples 3 and 4 was measured for the amount of adsorbed vapor when n-hexane or benzene was adsorbed and desorbed at a constant temperature of 10° C. or 20° C.

Figure 6:
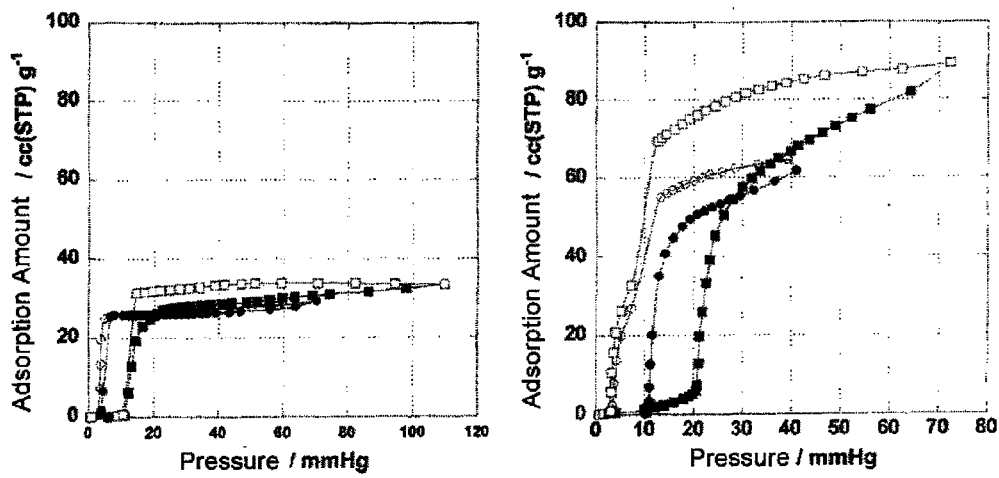
FIG. 6 shows the isothermic vapor adsorption curves of the organic carboxylic acid metal complex produced in Example 3 of the present invention.
Figure 7:
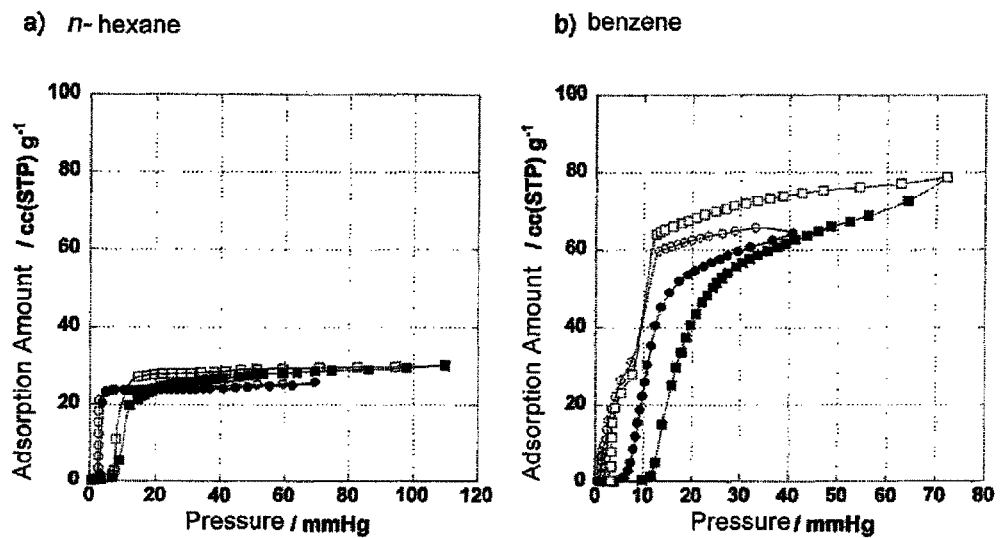
FIG. 7 shows the isothermic vapor adsorption curves of the organic carboxylic acid metal complex produced in Example 9 of the present invention.

The results are shown in FIGS. 6 and 7. In these figures, a) shows the results about n-hexane, and b) shows the results about benzene. Circles indicate the results at 10° C. and squares indicate the results at 20° C. Filled symbols indicate the results during adsorption process, and open symbols indicate the results during desorption process.

Characteristic reversible adsorption-desorption ability was observed, and both complexes showed almost the same adsorption behavior. These indicate that the complexes can function as an adsorbent for a wide variety of organic molecules having various shapes and properties, by virtue of the flexibility of the void structure. As for the adsorption curves, it was observed that the pressure required for the adsorption was higher at 20° C. than at 10° C., that is, the required pressure was shifted to the side of high pressure as the temperature increased. This suggests a thermodynamic correlation between the adsorption behaviors of the adsorbents and the temperature.

A characteristic feature in the adsorption behaviors is that a jump of adsorption is observed (this pressure is hereinafter referred to as critical pressure). Adsorption is scarcely observed at low pressures, and the jump of adsorption is first observed at the critical pressure. This is due to the bulk phase transition of the solid sample. The jump in the adsorption curve is due to the α-β phase transition induced by adsorption of vapor, and the flat part of the adsorption enthalpy is due to the co-existent state of α-β phases. The adsorption curve transits in a very narrow pressure region between the adsorption curves of α-β phases through the co-existent state of the two phases. With hexane or benzene, adsorption at a low pressure below the critical pressure is not observed. This is because that the void structure of the α phase is relatively thinly curved with respect to the molecular structure of the guest molecules, so that diffusion is difficult. Since the material is a crystal and the phase transition is induced by adsorption of the guest, a specific adsorption-desorption behavior is shown depending on the distribution of the guest molecules in the crystal. With these materials which are crystals having a small surface area with respect to the volume of the solid, adsorption is scarcely observed at a pressure below the critical pressure, that is, the materials have a function of sensing the vapor pressure (concentration) wherein adsorption is abruptly starts at the critical pressure. This is thought to be a phenomenon caused by the flexibility of the void structure and the phase transition phenomenon. Thus, adsorption characteristics having a high selectivity of vapor concentration and reversibility due to the flexibility of the void structure and the phase transition phenomenon of the present crystal materials were revealed.

Example 16

Absorption of Hydrogen Gas

Each of the organic carboxylic acid metal complexes produced in Examples 3, 9, 4 and 10 was measured for the amount of hydrogen when hydrogen gas was adsorbed and desorbed at a constant temperature of 77K.

Figure 8:
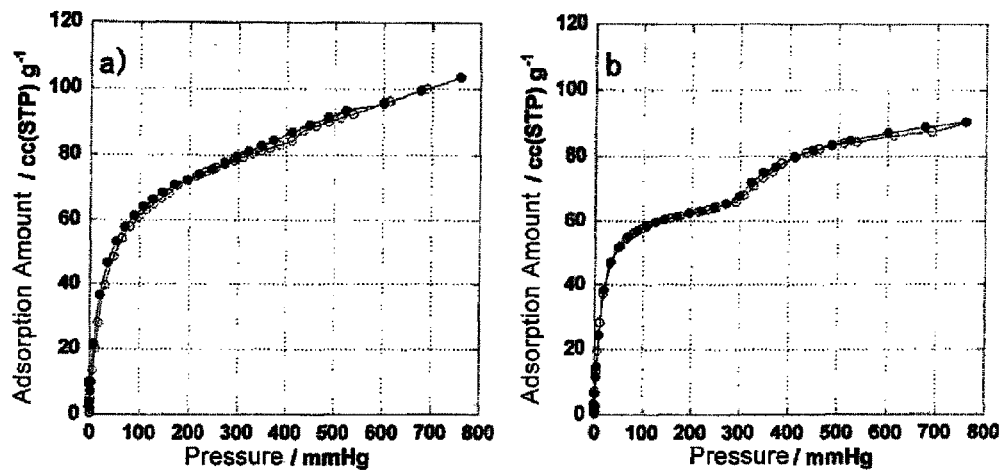
FIG. 8 shows hydrogen adsorption curves when hydrogen gas was absorbed by the organic carboxylic acid metal complexes produced in Examples 3, 9, 4 and 10 according to the present invention, respectively.
Figure 8:
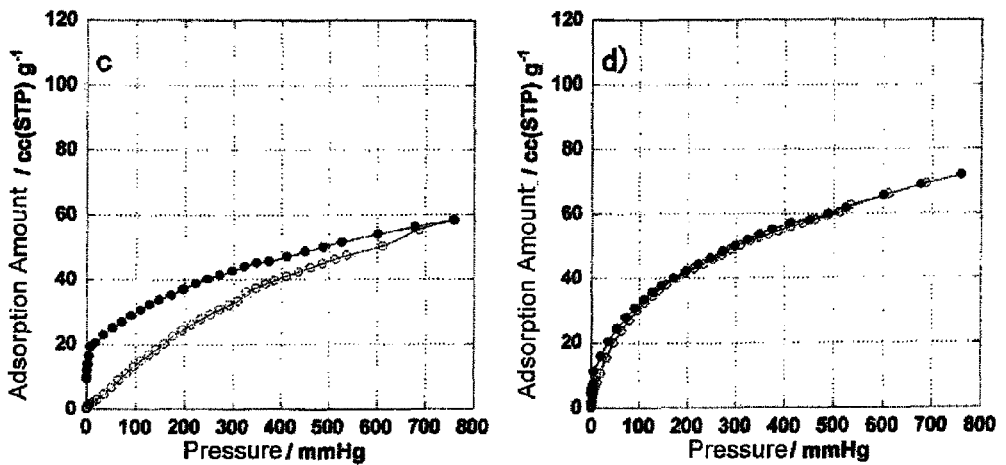

The results are shown in FIG. 8. In the figure, a), b), c) and d) show the results of the organic carboxylic acid metal complexes produced in Examples 3, 9, 4 and 10, respectively. Filled circles indicate the adsorption amount during the adsorption process and the open circles indicate the adsorption amount during the desorption process.

As shown in FIG. 8, a large amount of hydrogen can be absorbed by the organic carboxylic acid metal complexes. Further, it was observed that the diffusion was quick and adsorption equilibrium was reached in a short time.

Figure 9:
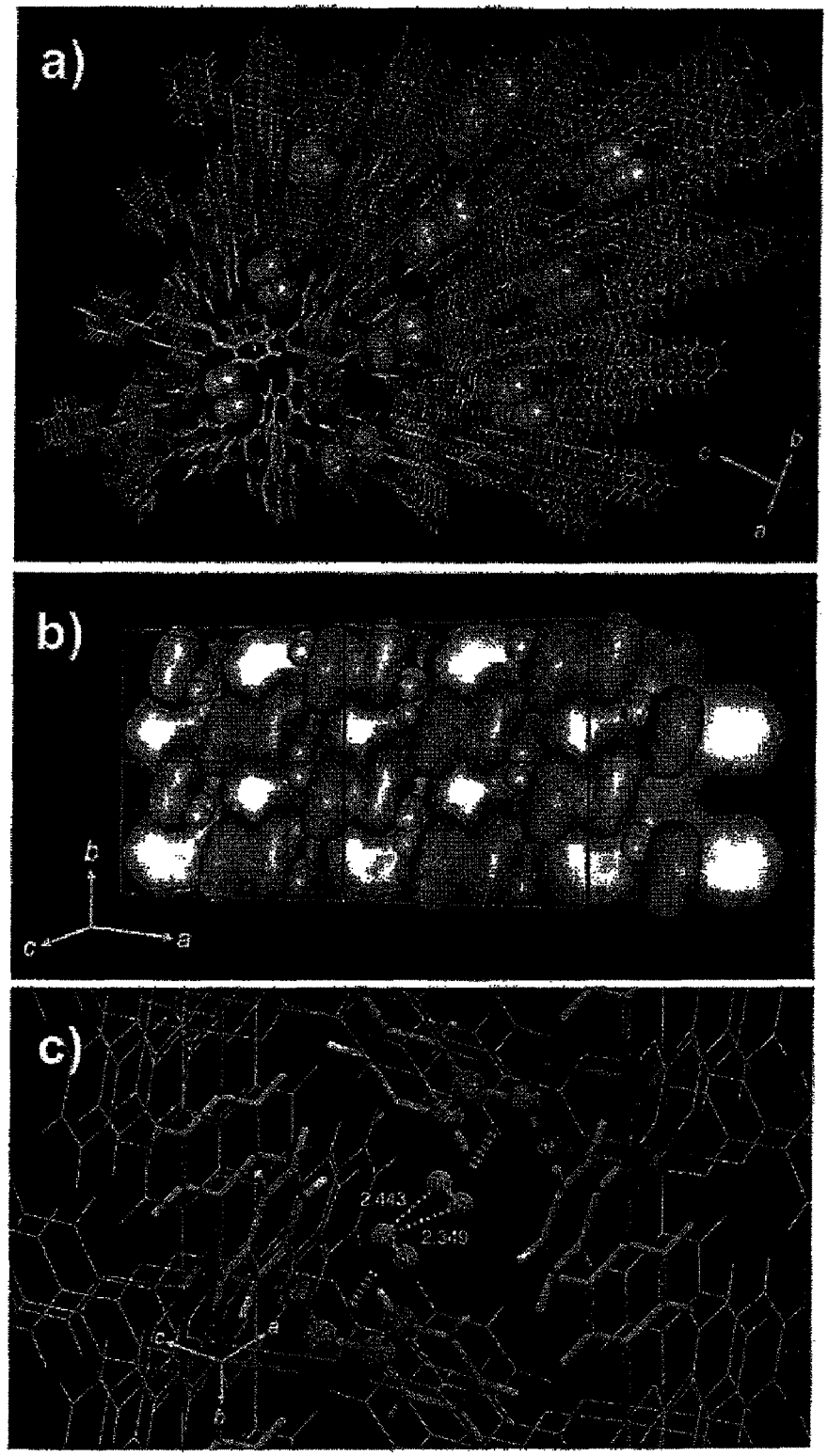
FIG. 9 schematically shows the crystal structure of the crystal of rhodium pyrazine benzoate produced in Example 9, in which hydrogen was adsorbed.

Further, the state of absorption of hydrogen was analyzed by subjecting to X-ray analysis the crystal of rhodium benzoate pyrazine produced in Example 9 in the state in which hydrogen was absorbed. The results are schematically shown in FIG. 9. The crystallographic parameters of the crystal in the state in which hydrogen was absorbed are shown in Table 5 below.

TABLE 5

| Composition Formula | $C_{32}H_{26}N_2O_8Rh_2$ |
|---|---|
| Molecular Weight | 1171.53 |
| Measuring Temperature [K] | 90K |
| Wavelength | 0.71073 Å |
| Crystal System | monoclinic system |
| Space Group | C2/c |
| a [Å] | 17.549 (4) |
| b [Å] | 9.591 (2) |
| c [Å] | 19.568 |
| α [degree] | 90 |

TABLE 5-continued

| | |
|---|---|
| β [degree] | 98.420 (4) |
| γ [degree] | 90 |
| Volume [Å$^3$] | 3258.0 (12) |
| Z | 4 |
| Density (Calcd.) [Mg/m$^3$] | 1.579 |
| Crystal Size [mm] | 0.25 × 0.23 × 0.04 |

Example 17

Adsorption of Mercury Vapor

The rhodium benzoate pyrazine single crystal produced in Example 9 (crystal size: 0.40×0.25×0.04 mm$^3$) was placed in a tightly closed glass vessel together with mercury, and the vessel was vacuumed with an oil rotary pump. The vessel was heated to 150° C. so as to expose the crystal to mercury vapor (vapor pressure: 2.8 mmHg). Seven days later, the vessel was cooled with water to normal temperature, and the crystal was taken out in the air. The crystal maintained the state of single crystal, and a clathrate crystal of mercury atoms was obtained. Yield: 100%

Figure 10:
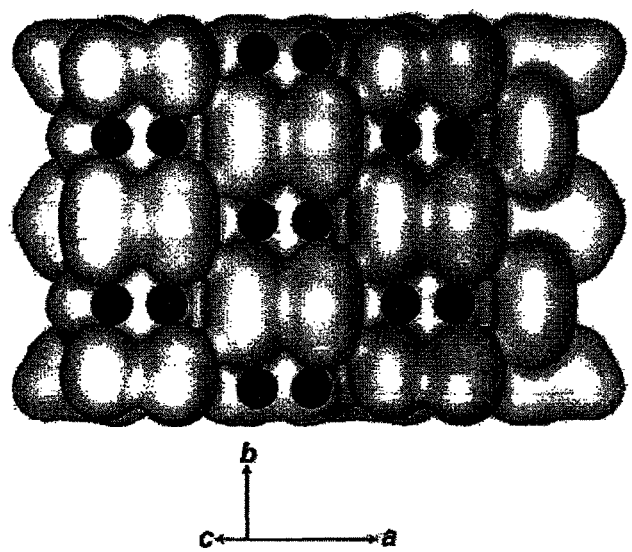
FIG. 10 schematically shows the crystal structure of the crystal of rhodium pyrazine benzoate produced in Example 9, in which mercury vapor was adsorbed.

The obtained clathrate crystal of mercury atoms was X-ray analyzed. The state of the crystal is schematically shown in FIG. 10. In the figure, filled circles are mercury atoms. The crystallographic parameters of the clathrate crystal of mercury atoms are shown in Table 6 below.

TABLE 6

| | |
|---|---|
| Composition Formula | C$_{32}$H$_{24}$Hg$_2$N$_2$O$_8$Rh$_2$ |
| Molecular Weight | 1171.53 |
| Measuring Temperature[K] | 90K |
| Wavelength | 0.71073 Å |
| Crystal System | monoclinic system |
| Space Group | C2/m |
| a [Å] | 17.573 (5) |
| b [Å] | 9.601 (3) |
| c [Å] | 12.202 (3) |
| α [degree] | 90 |
| β [degree] | 127.538 (4) |
| γ [degree] | 90 |
| Volume [Å$^3$] | 1632.4 (8) |
| Z | 2 |
| Density (Calcd.) [Mg/m$^3$] | 2.383 |
| Crystal Size [mm] | 0.40 × 0.25 × 0.04 |

Example 18

Details of Crystal Structure

Figure 11:
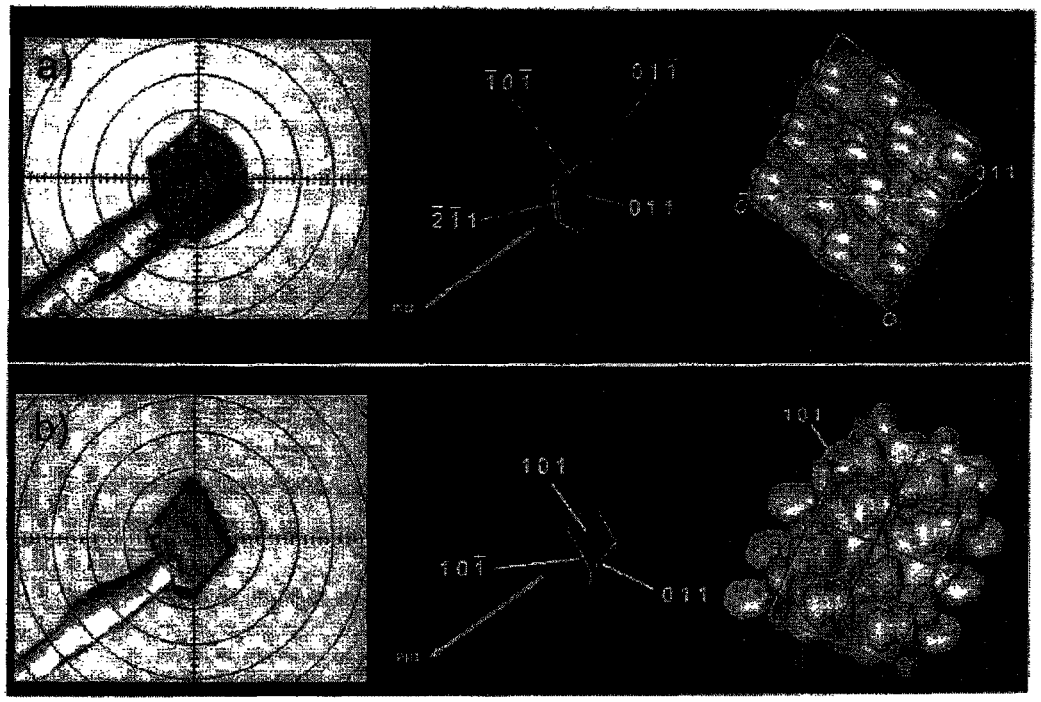
FIG. 11 are schematic views of stereoscopic micrographs of the single crystals produced in Examples 10 (a) and 4 (b), and the schematic views showing the indices of crystal plane, and the relationship between the crystal planes and the direction of channel, revealed by X-ray structure analysis of the single crystals.
Figure 12:
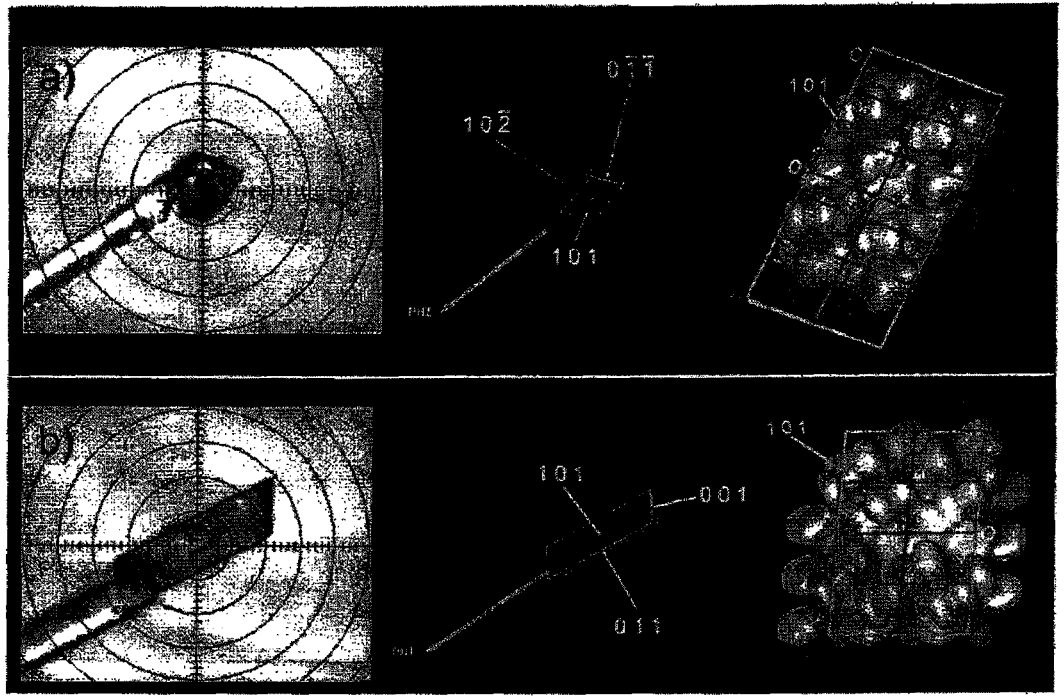
FIG. 12 are schematic views of stereoscopic micrographs of the single crystals produced in Examples 11 (a) and 5 (b), and the schematic views showing the indices of crystal plane, and the relationship between the crystal planes and the direction of channel, revealed by X-ray structure analysis of the single crystals.

Schematic views of stereoscopic micrographs of the single crystals produced in Examples 10 and 4, as well as the schematic views showing the indices of crystal plane, and the relationship between the crystal planes and the direction of channel, revealed by X-ray structure analysis of the single crystals, are shown in a) and b) in FIG. 11, respectively. Similarly, schematic views of stereoscopic micrographs of the single crystals produced in Examples 11 and 5, as well as the schematic views showing the indices of crystal plane, and the relationship between the crystal planes and the direction of channel, revealed by X-ray structure analysis of the single crystals, are shown in a) and b) in FIG. 12, respectively. In these figures, thick arrows indicate the channel structure.

Example 19

Change in Crystal Structure Before and after Adsorption of Carbon Dioxide (Part 1)

Figure 13:
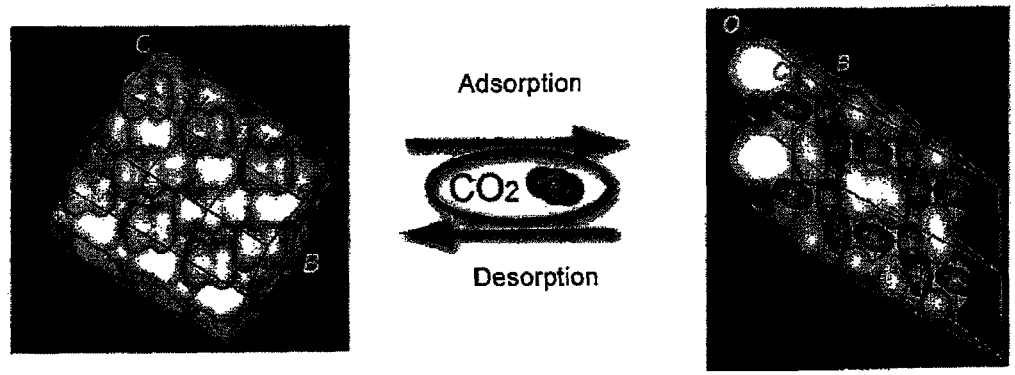
FIG. 13 are sectional views of the single crystal of 2-methylpyrazine benzoate complex produced in the Example of the present invention before and after the adsorption of carbon dioxide.
Figure 14:
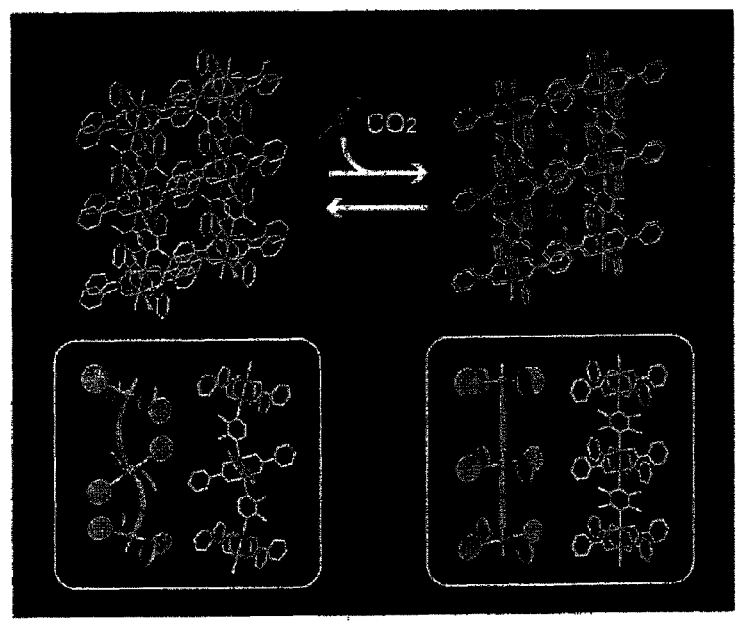
FIG. 14 schematically shows the change in the skeletal structure of the single crystal of 2-methylpyrazine benzoate complex produced in the Example of the present invention before and after the adsorption of carbon dioxide.
Figure 15:
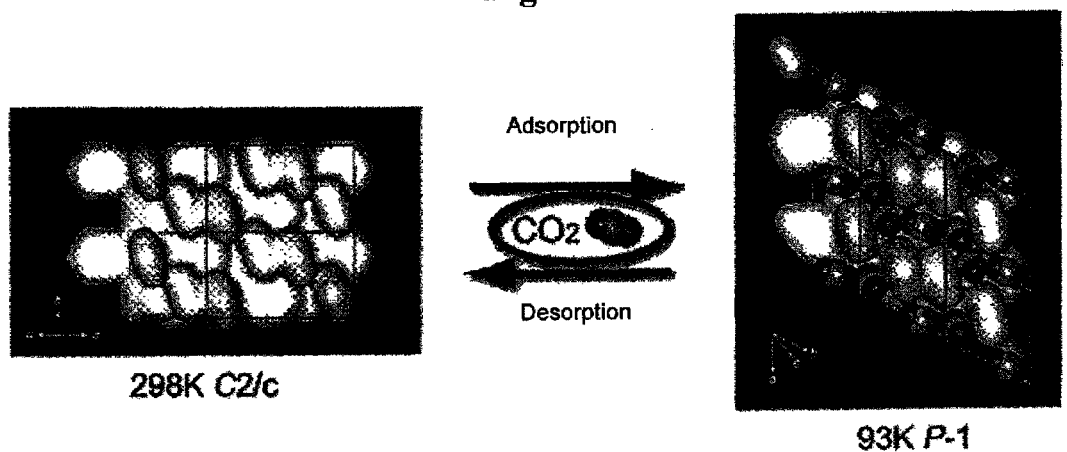
FIG. 15 are sectional views of the single crystal of pyrazine benzoate complex produced in the Example of the present invention before and after the adsorption of carbon dioxide.
Figure 16:
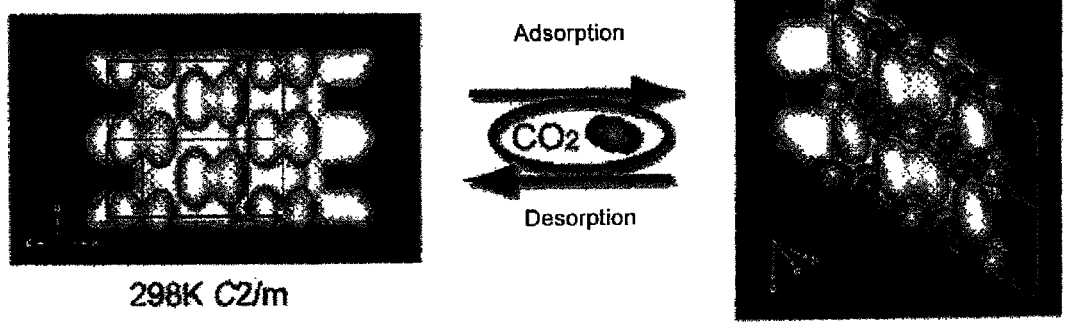
FIG. 16 schematically shows the change in the skeletal structure of the single crystal of pyrazine benzoate complex produced in the Example of the present invention before and after the adsorption of carbon dioxide.

Carbon dioxide gas was adsorbed by the 2-methylpyrazine benzoate complexes produced in Examples 4 and 10, respectively, and the changes in crystal structures before and after the adsorption were analyzed by X-ray analysis of the single crystals. Sectional views of the crystal of 2-methylpyrazine benzoate before and after the adsorption of carbon dioxide are schematically shown in FIG. 13. Similar results were obtained irrespective of whether the metal was copper (Example 4) or rhodium (Example 10). The change in the skeletal structure before and after the adsorption of carbon dioxide is schematically shown in FIG. 14. The sectional views of the crystals and the change in skeletal structures of the pyrazine benzoate complexes of Examples 3 and 9 are shown in FIGS. 15 and 16, respectively.

With each of the 2-methylpyrazine benzoate complexes of Examples 4 and 10, the structure before adsorption was an integration of zigzag one-dimensional strands folded by steric hindrance of the methyl groups on the 2-methylpyrazine rings. After the adsorption, the structure of the molecular strands changed to straight strands, and one-dimensional channels are generated and $CO_2$ molecules are clathrated therein. By the introduction of a substituent group(s), change in solid structure can be controlled.

Table 7 shows the change in the $V_{cell}/Z$ and porosity before and after the $CO_2$ clathration at 90 K. The changes in $V_{cell}/Z$ were: complex (2a) of Example 10: 813.1→893.3 Å$^3$ (9.0% increase); complex (2b) of Example 4: 812.9→900.1 Å$^3$ (9.7% increase), so that increase in the cell volume was observed by clathrating $CO_2$ molecules. Comparing the void volumes before and after clathration, the void volumes increased twice or more with both 2a and 2b, so that the volume of the spaces in which gas is adsorbed is drastically changed by the change of the solid structure.

TABLE 7

| Complex | 2a | 2a · 3($CO_2$) | 2b | 2b · 3($CO_2$) |
|---|---|---|---|---|
| $V_{cell}/Z$ (Å$^3$) | 813.1 | 893.3 | 812.9 | 900.1 |
| Void Volume (Å$^3$/%) | 106.1/6.5 | 152.9/17.1*[1] | 137.0/8.4 | 158.7/17.6*[1] |

*[1])calculated excluding clathrated $CO_2$

Example 20

Change in Crystal Structure Before and after Adsorption of Carbon Dioxide (Part 2)

Figure 17:
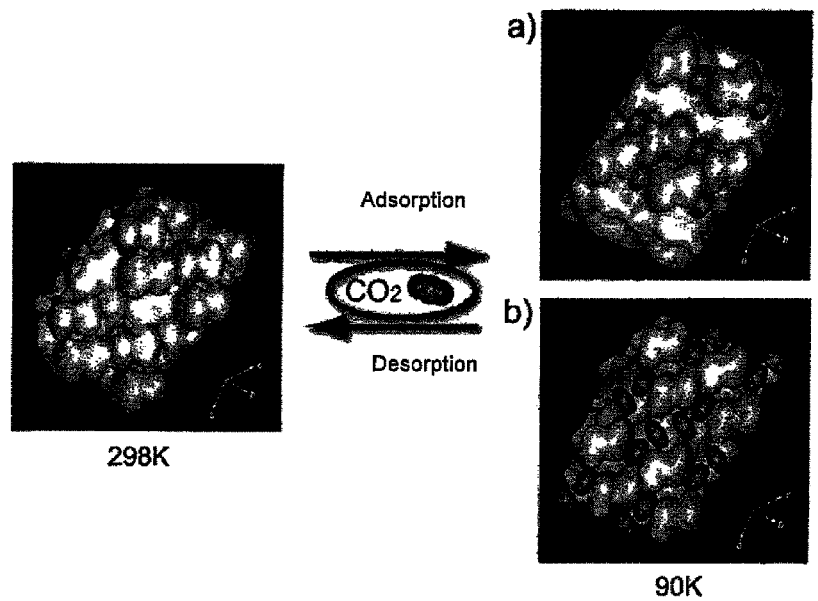
FIG. 17 are sectional views of the complex produced in Example 11 of the present invention before and after the adsorption of carbon dioxide.

The complex produced in Example 11 was examined for the states of the cross section of the crystal before and after the adsorption of carbon dioxide by X-ray analysis as in Example 19. The results are schematically shown in FIG. 17.

As for the state of alignment of the $CO_2$ in the channel, unlike the one-dimensional alignment in the above-described crystals, the $CO_2$ molecules formed tetramers. It has a character that the void structure in the solid can be changed and, in turn, that the guest molecules-adsorbed structure in the crystal can be controlled by the introduction of a substituent group(s).

Example 21

Adsorption and Desorption of Carbon Dioxide

Figure 18:
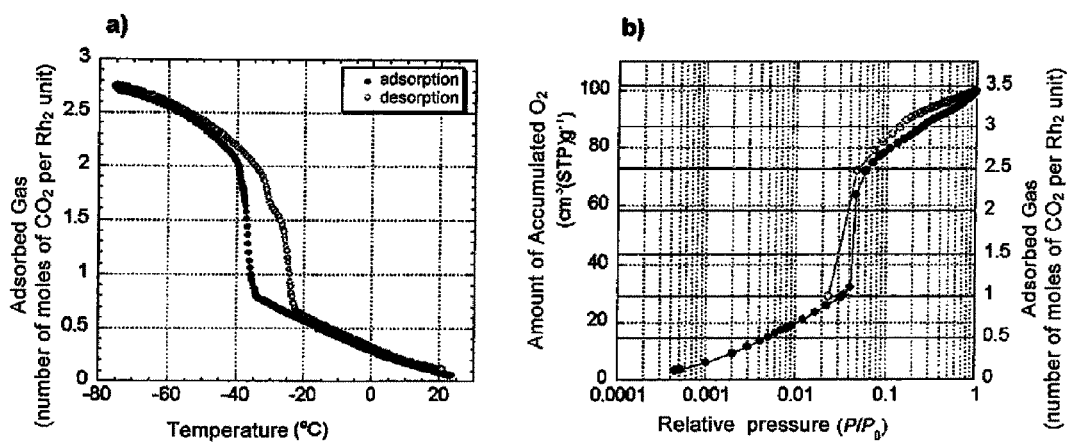
FIG. 18 shows the results of the measurements of adsorption amount of carbon dioxide by the complex produced in Example 10, measured at a constant temperature or under a constant pressure.

The complex (2a) produced in Example 10 and the complex (2b) produced in Example 4 were measured for the adsorption amount of carbon dioxide at a constant temperature or under a constant pressure. The isobaric adsorption measurement was carried out at 1 atm, and the isothermic measurement was carried out at −70° C. The results are shown in FIGS. 18 (2a) and 19 (2b), respectively. In each of the figures, filled circles indicate the adsorption amount during the adsorption process and the open circles indicate the adsorption amount during the desorption process.

Figure 19:
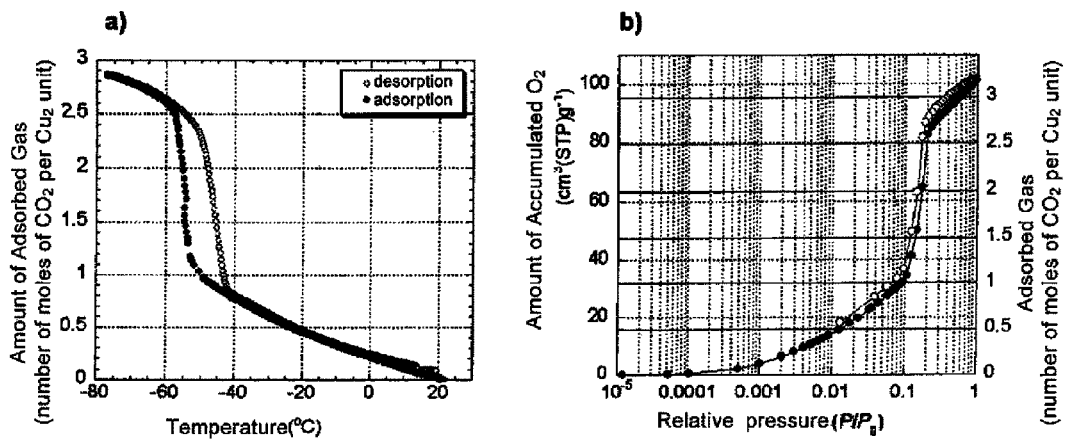
FIG. 19 shows the results of the measurements of adsorption amount of carbon dioxide by the complex produced in Example 4, measured at a constant temperature or under a constant pressure.

As shown in FIGS. 18 and 19, with each of both complexes, the adsorption and desorption were reversible, and specific gas-adsorption characteristics were shown by the crystal structure and change thereof. Thus, it was shown that the crystals can be used as a material for separation and concentration of carbon dioxide, and for storage of carbon dioxide.

Example 22

Adsorption and Desorption of Oxygen Gas

Each of the organic carboxylic acid metal complexes produced in Examples 10, 4, 11 and 5 was measured for the amount of adsorbed oxygen gas at a constant temperature of 77K. The results are shown in a), b), c) and d) in FIG. 10, respectively. In each of the figures, filled circles indicate the adsorption amount during the adsorption process and the open circles indicate the adsorption amount during the desorption process.

Figure 20:
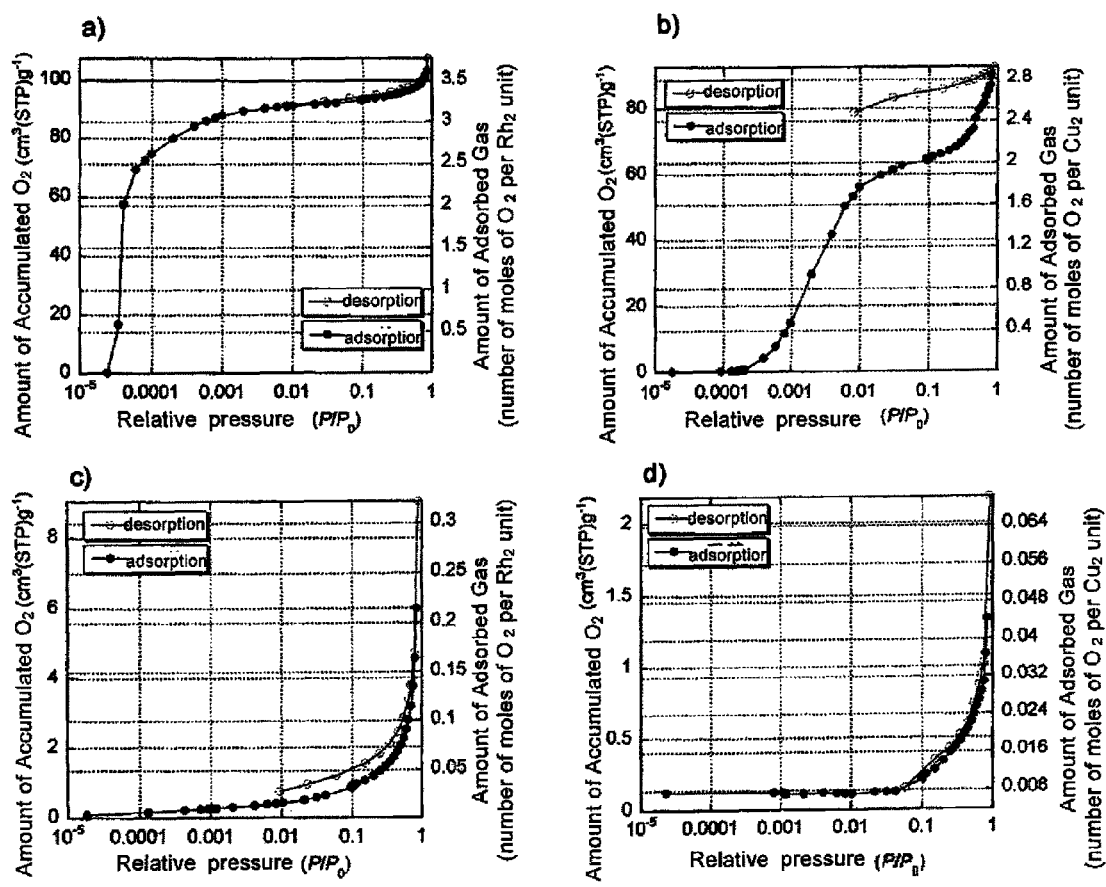
FIG. 20 shows the results of the measurements of the amount of oxygen gas at a constant temperature of 77K adsorbed in each of the complex (a) produced in Example 10, the complex (b) produced in Example 4, the complex (c) produced in Example 11, and the complex (d) produced in Example 5, respectively.

As shown in FIG. 20, with each of the complexes, the adsorption and desorption were reversible, and specific gas-adsorption characteristics were shown by the crystal structure and change thereof. Thus, it was shown that the crystals can be used as a material for separation and concentration of oxygen gas, and for storage of oxygen gas.

Example 23

Adsorption and Desorption of Nitrogen Gas

Each of the organic carboxylic acid metal complexes produced in Examples 10, 4, 11 and 5 was measured for the amount of adsorbed nitrogen monoxide gas at a constant temperature of 77K. The results are shown in a), b), c) and d) in FIG. 21, respectively. In each of the figures, filled circles indicate the adsorption amount during the adsorption process and the open circles indicate the adsorption amount during the desorption process.

Figure 21:
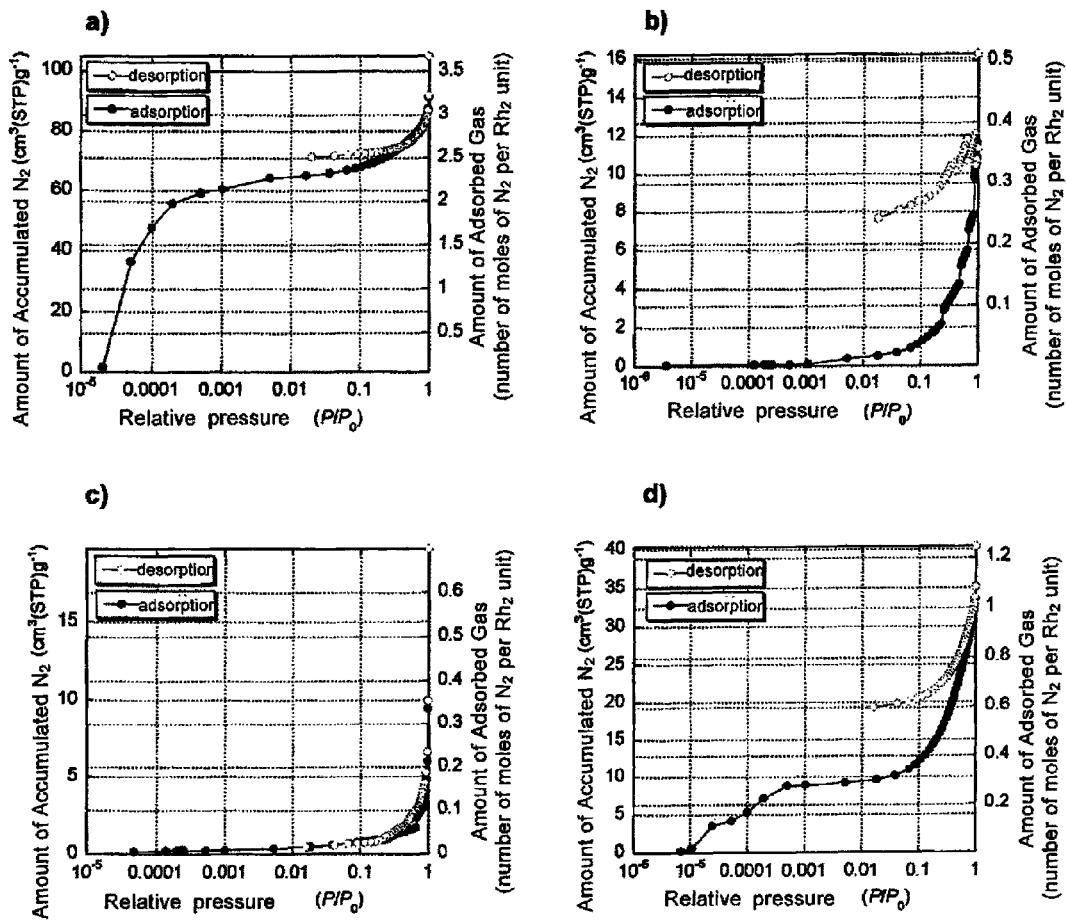
FIG. 21 shows the results of the measurements of the amount of nitrogen gas at a constant temperature of 77K adsorbed in each of the complex (a) produced in Example 10, the complex (b) produced in Example 4, the complex (c) produced in Example 11, and the complex (d) produced in Example 5, respectively.

As shown in FIG. 21, with each of the complexes, the adsorption and desorption were reversible, and specific gas-adsorption characteristics were shown by the crystal structure and change thereof. Thus, it was shown that the crystals can be used as a material for separation and concentration of nitrogen gas, and for storage of nitrogen gas.

Example 24

Adsorption and Desorption of Nitrogen Monoxide Gas

Figure 22:
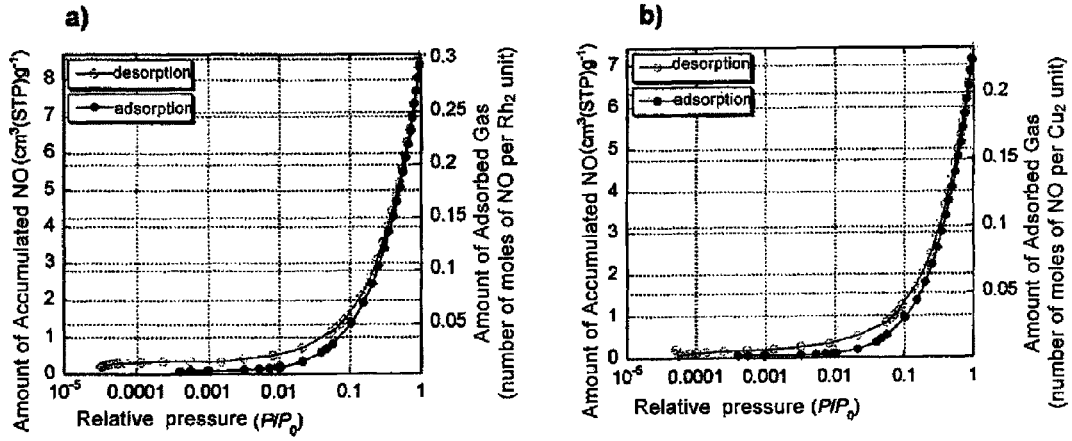
FIG. 22 shows the results of the measurements of the amount of nitrogen monoxide gas at a constant temperature of 20° C. adsorbed in each of the complex (a) produced in Example 10 and in the complex (b) produced in Example 4, respectively.

Each of the organic carboxylic acid metal complexes produced in Examples 10 and 4 was measured for the amount of adsorbed nitrogen gas at a constant temperature of 20° C. The results are shown in a) and b) in FIG. 22, respectively. In each of the figures, filled circles indicate the adsorption amount during the adsorption process and the open circles indicate the adsorption amount during the desorption process.

As shown in FIG. 21, with each of the complexes, the adsorption and desorption were reversible, and specific gas-adsorption characteristics were shown by the crystal structure and change thereof. Thus, it was shown that the crystals can be used as a material for separation and concentration of nitrogen monoxide gas, and for storage of nitrogen monoxide gas.

The invention claimed is:

1. An organic carboxylic acid complex produced by a method for one-dimensionally aligning metal atoms in a single line, said method comprising absorbing a metal vapor with an organic carboxylic acid metal complex constituted by recurring units of the Formula [I]:

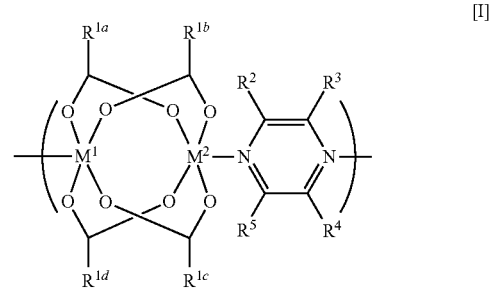

wherein $M^1$ and $M^2$ are each independently a metal which can be bivalent; $R^{1a}$, $R^{1b}$, $R^{1c}$ and $R^{1d}$ are each independently an organic group having a conjugated system; $R^2$, $R^3$, $R^4$ and $R^5$ are each independently hydrogen, $C_1$-$C_4$ alkyl or $C_1$-$C_4$ alkenyl, said organic carboxylic acid complex harboring in a channel structure metal atoms as a guest, said metal atoms being aligned one-dimensionally in a single line.

2. The organic carboxylic acid complex according to claim 1, wherein said $R^{1a}$, $R^{1b}$, $R^{1c}$ and $R^{1d}$ are each independently phenyl group which is optionally substituted.

3. The organic carboxylic acid complex according to claim 1, wherein said $M^1$ and $M^2$ are each independently at least one selected from the group consisting of manganese, iron, cobalt, nickel, copper, zinc, ruthenium, rhodium, chromium, molybdenum, palladium and tungsten.

4. The organic carboxylic acid complex according to claim 1, wherein said $M^1$ and $M^2$ are the same metal, and said $R^{1a}$, $R^{1b}$, $R^{1c}$ and $R^{1d}$ are the same organic group.

5. The organic carboxylic acid complex according to claim 1, wherein said $R^{1a}$, $R^{1b}$, $R^{1c}$ and $R^{1d}$ are phenyl, said $R^2$, $R^3$, $R^4$ and $R^5$ are each independently hydrogen or $C_1$-$C_4$ alkyl, and said $M^1$ and $M^2$ are copper or rhodium.

6. The organic carboxylic acid complex according to claim 1, wherein said organic carboxylic acid metal complex is in the form of a single crystal(s).

* * * * *